United States Patent
Kamiyama et al.

[11] Patent Number: 5,948,774
[45] Date of Patent: Sep. 7, 1999

[54] CEPHEM COMPOUNDS, THEIR PRODUCTION AND USE

[75] Inventors: Keiji Kamiyama; Kenji Okonogi; Akio Miyake, all of Osaka, Japan

[73] Assignee: Takeda Chemical Industries, Ltd., Osaka, Japan

[21] Appl. No.: 08/836,424

[22] PCT Filed: May 28, 1996

[86] PCT No.: PCT/JP96/01436

§ 371 Date: Jul. 29, 1997

§ 102(e) Date: Jul. 29, 1997

[87] PCT Pub. No.: WO96/34851

PCT Pub. Date: Dec. 5, 1996

[30] Foreign Application Priority Data

May 29, 1995 [JP] Japan .................................. 7/130287

[51] Int. Cl.⁶ ...................... C07D 501/24; A61K 31/545
[52] U.S. Cl. ............................................ 514/203; 540/225
[58] Field of Search .............................. 514/203; 540/225

[56] References Cited

U.S. PATENT DOCUMENTS 4,761,410  8/1988  Takaya ..................................... 540/225

FOREIGN PATENT DOCUMENTS

| 0 111 281 | 6/1984 | European Pat. Off. . |
| 0 630 899 A1 | 12/1994 | European Pat. Off. . |
| 0 700 916 A1 | 3/1996 | European Pat. Off. . |
| 6-135972 | 5/1994 | Japan . |
| 2 183 629 | 6/1987 | United Kingdom . |
| 96/23798 | 8/1996 | WIPO . |

*Primary Examiner*—Mark L. Berch
*Attorney, Agent, or Firm*—Wenderoth, Lind & Ponack, L.L.P.

[57] ABSTRACT

Cephem compounds of the formula:

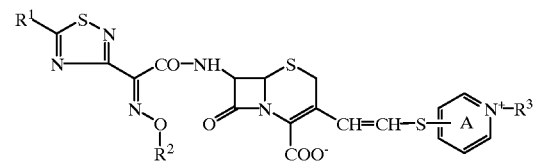

wherein $R^1$ is an optionally protected amino group; $R^2$ is a fluoro-lower alkyl group; and the ring A may have further substituent(s), or their esters or salts, show broad and excellent antibacterial activities and are useful as antibacterial agents.

17 Claims, No Drawings

CEPHEM COMPOUNDS, THEIR PRODUCTION AND USE

BACKGROUND OF THE INVENTION

1. Field of the Invention

This invention relates to a novel cephem compound having excellent antibacterial activities on a broad range of Gram-positive and Gram-negative bacteria, especially *Staphylococcus aureus* and methicillin-resistant *Staphylococcus aureus* (MRSA), to a method of producing the compound and to an antibacterial composition containing the compound.

2. Description of Related Art

Various cephem compounds having, at the 7-position, 2-(5-amino-1,2,4-thiadiazol-3-yl)-2(Z)-oxyiminoacetamido group, and having, at the 3-position, pyridiniothiovinyl group, have been reported in JPA S59(1984)-130292 and JPA H6(1994)-206886. In JPA S59(1984)-130292, however, while aminothiadiazolyl (lower) alkanoylamino having a lower alkoxyimino as the substituent at the 7-position of the cephem compound is disclosed, no description is found that the lower alkoxy may optionally be substituted with fluorine. And, in JPA H6(1994)-206886, only 2-(5-amino-1,2,4-thiadiazol-3-yl) or (2-aminothiazol-4-yl)-2(Z)-hydroxyiminoacetamido group is described as the substituents at the 7-position of the cephem compound, and no description on cephem compounds having 2-(5-amino-1,2,4-thiadiazol-3-yl)-2(Z)-fluorine substituted lower alkyloxyiminoacetamido group and their effect is found at all.

So far known cephem compounds are not sufficiently satisfactory in the range and strength of antibacterial activities, especially, in conventional cephalosporin compounds, antibacterial activities against *Staphylococcus aureus* and methicillin resistant *Staphylococcus aureus* (MRSA) are not sufficiently satisfactory, and creation of novel compounds overcoming this point has been desired.

SUMMARY OF THE INVENTION

Taking the foregoing circumstances into consideration, the present inventors conducted diligent studies extensively and synthesized, for the first time, a cephem compound characterized by having, at the 3-position of its cephem nucleus, a group of the formula

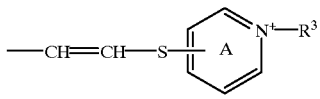

wherein $R^3$ is an optionally substituted hydrocarbon group, and the ring A may optionally have further substituent(s), and, at the 7-position, a group of the formula:

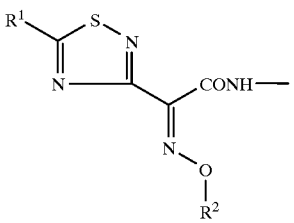

wherein $R^1$ is an optionally protected amino group, and $R^2$ is a fluoro-lower-alkyl group, or an ester or salt thereof, and further found that the compound thus synthesized showed unexpectedly broadly excellent antibacterial activities against Gram-negative bacteria and against Gram-positive bacteria including *Staphylococcus aureus* and MRSA. Based on these findings, the present invention was accomplished.

More specifically, the present invention relates to:

(1) a cephem compound of the formula:

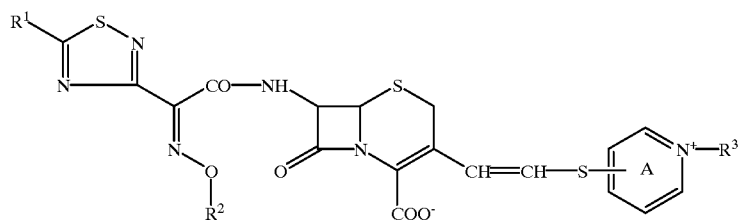

[I]

wherein $R^1$ is an optionally protected amino group; $R^2$ is a fluoro-lower-alkyl group; $R^3$ is an optionally substituted hydrocarbon group; and the ring A may optionally have further substituent(s) or an ester or salt thereof, (2) the cephem compound of the formula:

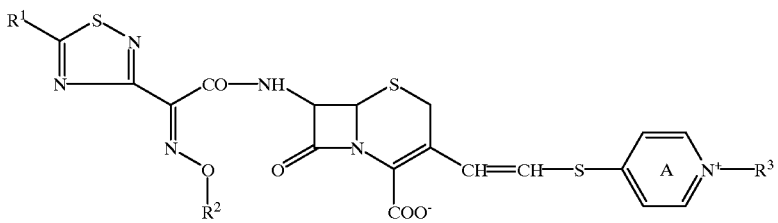
[I-a]

wherein symbols are of the same meaning as described above, or an ester or salt thereof.

(3) a method of producing the compound described in (1) above, which comprises reacting a compound of the formula:

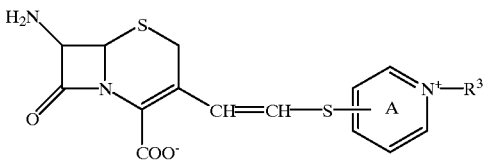
[II]

wherein symbols are of the same meaning as defined above, or an ester or salt thereof, with carboxylic acid of the formula:

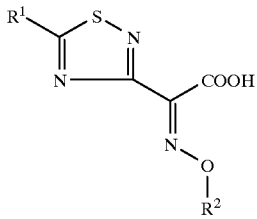

wherein symbols are of the same meaning as defined above, or a salt or reactive derivative thereof, then, upon necessity, by removing the protective group. (4) a method of producing the compound described in (1) above, which comprises reacting a compound of the formula:

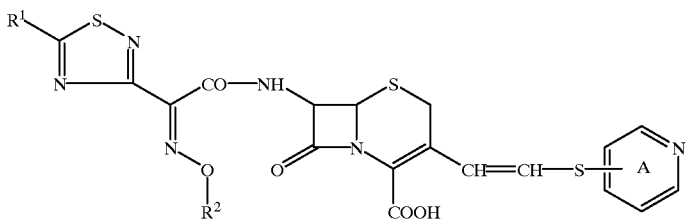

wherein symbols are of the same meaning as defined above, or an ester or salt thereof, with a compound of the formula, $R^3$—X, (wherein X is a leaving group and $R^3$ is of the same meaning as defined above, then, upon necessity, by removing the protective group, (5) an antibacterial composition which comprises an effective amount of a compound described in (1) above and pharmaceutically acceptable carrier, diluent or excipient, and (6) a method for treating and/or preventing bacterial infection which comprises administering an effective amount of a compound described in (1) above optionally together with a pharmaceutically acceptable carrier, diluent or excipient to a patient suffering from a bacterial infection, and (7) use of a compound described in (1) above for the manufacture of an antibacterial composition.

The cephem compound in the present specification includes a group of compounds named on the basis of "cepham" disclosed in "The Journal of The American Chemical Society" Vol. 84, p.3400 (1962), which means a compound, among the cepham compounds, having a double bond at the 3,4-positions.

Incidentally, the compounds of this invention include the compound of the formula [I] showing the free form or an ester or salt thereof (a salt of the compound [I] or a salt of the ester of the compound [I]). In the present specification, hereinafter, unless otherwise specified, the compound of the formula [I] shown in the free form or an ester or salt thereof is simply referred to as the compound [I], the antibacterial compound [I] or the compound represented by the formula [I]. Accordingly, the compound [I] in the present specification include, usually, the free form as well as an ester or salt thereof. This is applicable as well to the starting compounds, for example, compounds [I-a], [I-b], [II], [III], [V], [VI], [IX·, [X], [XI] and [XII] described in the following.

DETAILED DESCRIPTION OF THE PREFERRED EMBODIMENTS $R^1$ stands for an optionally protected amino group. In the fields of β-lactam and peptide, amino-protective groups have been sufficiently studied, and the method of protecting amino group has been established. In the present invention also, as amino-protective groups, those conventional ones can be adequately employed. Examples of amino-protective groups to be employed include optionally substituted $C_{1-6}$alkanoyl groups, optionally substituted $C_{3-5}$alkenoyl groups, optionally substituted $C_{6-10}$aryl-carbonyl groups, heterocyclic carbonyl groups, optionally substituted $C_{1-10}$alkylsulfonyl groups, optionally substituted $C_{6-10}$arylsulfonyl groups, substituted oxycarbonyl groups, optionally substituted carbamoyl groups, optionally substituted thiocarbamoyl groups, optionally substituted $C_{6-10}$aryl-methyl groups, optionally substituted di-$C_{6-10}$aryl-methyl groups, optionally substituted tri-$C_{6-10}$aryl-methyl groups, optionally substituted $C_{6-10}$aryl-methylene groups, optionally substituted $C_{6-10}$arylthio group, substituted silyl groups, 2-$C_{1-10}$alkoxy-carbonyl-1-methyl-1-ethenyl groups and groups represented by the formula M'OCO— (wherein M' stands for an alkali metal).

As "optionally substituted $C_{1-6}$alkanoyl groups", use is made of, for example, $C_{1-6}$alkanoyl groups which may optionally be substituted with 1 to 3 substituents selected from halogen, oxo, $C_{1-6}$alkoxy, $C_{1-6}$alkanoyl, $C_{6-10}$aryl, halogeno $C_{6-10}$aryl, $C_{6-10}$aryloxy, halogeno $C_{6-10}$aryloxy and $C_{6-10}$arylthio. More specifically, use is made of, for example, formyl, acetyl, propionyl, butyryl, valeryl, pivaloyl, succinyl, glutaryl, monochloroacetyl, dichloroacetyl, trichloroacetyl, monobromoacetyl, monofluoroacetyl, difluoroacetyl, trifluoroacetyl, monoiodoacetyl, acetoacetyl, 3-oxobutyryl, 4-chloro-3-oxobutyryl, phenylacetyl, p-chlorophenylacetyl, phenoxyacetyl and p-chlorophenoxyacetyl.

As "optionally substituted $C_{3-5}$alkenoyl groups", use is made of, for example, $C_{3-5}$alkenoyl groups optionally substituted with 1 to 3 substituents selected from halogen and $C_{6-10}$aryl, more specifically, for example, acryloyl, crotonoyl, maleoyl, cinnamoyl, p-chlorocinnamoyl and β-phenylcinnamoyl.

As "optionally substituted $C_{6-10}$aryl-carbonyl groups", use is made of, for example, $C_{6-10}$aryl-carbonyl groups optionally substituted with 1 to 3 substituents selected from halogen, nitro, hydroxy, $C_{1-6}$alkyl and $C_{1-6}$alkoxy, more specifically, for example, benzoyl, naphthoyl, phthaloyl, p-toluoyl, p-tert-butylbenzoyl, p-hydroxybenzoyl, p-methoxybenzoyl, p-tert-butoxybenzoyl, p-chlorobenzoyl and p-nitrobenzoyl.

"Heterocyclic group" in "heterocyclic carbonyl group" means a group formed by removing one hydrogen atom linked to carbon atom of the heterocyclic ring. The heterocyclic ring means a 5- to 8-membered ring containing 1 to several numbers, preferably 1 to 4 hetero-atoms such as nitrogen atom which may be oxidized, oxygen atom and sulfur atom, or a condensed ring thereof. As such heterocyclic group, use is practically made of, for example, 2- or 3-pyrrolyl; 3-, 4- or 5-pyrazolyl; 2-, 4- or 5-imidazolyl; 1,2,3- or 1,2,4-triazolyl; 1H- or 2H-tetrazolyl; 2- or 3-furyl; 2- or 3-thienyl; 2-, 4- or 5-oxazolyl; 3, 4- or 5-isoxazolyl; 1,2,3-oxadiazol-4-yl or 1,2,3-oxadiazol-5-yl; 1,2,4-oxadiazol-3-yl or 1,2,4-oxadiazol-5-yl; 1,2,5- or 1,3,4-oxadiazolyl; 2-, 4- or 5-thiazolyl; 3-, 4- or 5-isothiazolyl; 1,2,3-thiadiazol-4-yl or 1,2,3-thiadiazol-5-yl; 1,2,4-thiadiazol-3-yl or 1,2,4-thiadiazol-5-yl; 1,2,5- or 1,3,4-thiadiazolyl; 2- or 3-pyrrolidinyl; 2-, 3- or 4-pyridyl; 2-, 3- or 4-pyridyl-N-oxido; 3- or 4-pyridazinyl; 3- or 4-pyridazinyl-N-oxido; 2-, 4- or 5-pyrimidinyl; 2-, 4- or 5-pyrimidinyl-N-oxido; pyrazinyl; 2-, 3- or 4-piperidinyl; piperazinyl; 3H-indol-2-yl or 3H-indol-3-yl; 2-, 3- or 4-pyranyl; 2-, 3- or 4-thiopyranyl; benzopyranyl; quinolyl; pyrido[2,3-d]pyrimidyl; 1,5-, 1,6-, 1,7-, 1,8-, 2,6- or 2,7-naphthyridyl; thieno[2,3-d]pyridyl; pyrimidopyridyl; pyrazinoquinolyl; and benzopyranyl.

As "optionally substituted $C_{1-10}$alkylsulfonyl group", use is made of a $C_{1-10}$alkylsulfonyl group optionally substituted with 1 to 3 substituents selected from, for example, halogen, $C_{6-10}$aryl and $C_{6-10}$aryloxy. More specifically, use is made of, for example, methanesulfonyl, ethanesulfonyl and camphor sulfonyl.

As "optionally substituted $C_{6-10}$arylsulfonyl group", use is made of, a $C_{6-10}$arylsulfonyl group optionally substituted with 1 to 3 substituents selected from, for example, halogen, nitro, $C_{1-6}$alkyl and $C_{1-6}$alkoxy. More specifically, for example, benzenesulfonyl, naphthalenesulfonyl, p-toluenesulfonyl, p-tert-butylbenzenesulfonyl, p-methoxybenzenesulfonyl, p-chlorobenzensulfonyl and p-nitrobenzenesulfonyl.

Examples of "substituted oxycarbonyl group" include, in addition to a $C_{1-10}$alkoxy-carbonyl group, a $C_{3-10}$cycloalkoxy-carbonyl group, a $C_{5-10}$cross-linked cyclic hydrocarbonoxy-carbonyl group, a $C_{2-10}$-alkenyloxycarbonyl group, a $C_{6-10}$aryloxy-carbonyl group or a $C_{7-19}$aralkyloxy-carbonyl group, those further having 1 to 3 substituents selected from $C_{1-6}$alkoxy, $C_{1-6}$alkanoyl, $C_{1-10}$alkanoyloxy, $C_{1-10}$alkoxy-carbonyloxy, $C_{3-10}$cycloalkyloxy-carbonyloxy, a substituted silyl group (the substituted silyl group described later, e.g. trimethyl silyl and tert-butyl dimethyl silyl), $C_{1-6}$alkylsulfonyl, halogen, cyano, $C_{1-6}$alkyl and nitro. Practically, use is made of, for example, methoxymethyloxycarbonyl, acetylmethyloxycarbonyl, 2-trimethylsilylethoxycarbonyl, 2-methanesulfonylethoxycarbonyl, 2,2,2-trichloroethoxycarbonyl, 2-cyanoethoxycarbonyl, aryloxycarbonyl, p-methylphenoxycarbonyl, p-methoxyphenoxycarbonyl, p-chlorophenoxycarbonyl, m-nitrophenoxycarbonyl, p-methylbenzyloxycarbonyl, p-methoxybenzyloxycarbonyl, p-chlorobenzyloxycarbonyl, p-nitrobenzyloxycarbonyl, o-nitrobenzyloxycarbonyl and 3,4-dimethoxy-6-nitrobenzyloxycarbonyl.

As "optionally substituted carbamoyl group", use is made of a carbamoyl group optionally substituted with one or two substituents selected from, for example, $C_{1-6}$alkyl, $C_{6-10}$aryl, $C_{1-6}$alkanoyl, $C_{6-10}$arylcarbonyl and $C_{1-6}$alkoxy-phenyl groups. More specifically, use is made of, for example, N-methylcarbamoyl, N-ethylcarbamoyl, N,N-dimethylcarbamoyl, N,N-diethylcarbamoyl, N-phenylcarbamoyl, N-acetylcarbamoyl, N-benzoylcarbamoyl and N-(p-methoxyphenyl)carbamoyl.

As "optionally substituted thiocarbamoyl group", use is made of a thiocarbamoyl group optionally substituted with one or two substituents selected from, for example, $C_{1-6}$alkyl and $C_{6-10}$aryl, as exemplified by thiocarbamoyl, N-methylthiocarbamoyl and N-phenylthiocarbamoyl.

As "optionally substituted $C_{6-10}$aryl-methyl group", use is made of a $C_{6-10}$aryl-methyl group optionally substituted with 1 to 3 substituents selected from, for example, halogen, nitro, $C_{1-6}$alkyl and $C_{1-6}$alkoxy. More specifically, for example, benzyl, naphthylmethyl, p-methylbenzyl, p-methoxybenzyl, p-chlorobenzyl and p-nitrobenzyl are used.

As "optionally substituted di-$C_{6-10}$aryl-methyl group", use is made of a di-$C_{6-10}$aryl-methyl group optionally substituted with 1 to 3 substituents selected from, for example, halogen, nitro, $C_{1-6}$alkyl and $C_{1-6}$alkoxy. More specifically, for example, benzhydryl and di(p-tolyl)methyl are used.

As "optionally substituted tri-$C_{6-10}$aryl-methyl group", use is made of a tri-$C_{6-10}$aryl-methyl group optionally substituted with 1 to 3 substituents selected from, for example, halogen, nitro, $C_{1-6}$alkyl and $C_{1-6}$alkoxy. More specifically, for example, trityl and tri(p-tolyl)methyl are used.

As "optionally substituted $C_{6-10}$aryl-methylene group", use is made of, a $C_{6-10}$aryl-methylene group optionally substituted with 1 to 3 substituents selected from, for example, halogen, nitro, $C_{1-6}$alkyl and $C_{1-6}$alkoxy. More specifically, for example, benzylidene, p-methylbenzylidene and p-chlorobenzylidene are used.

As "optionally substituted $C_{6-10}$arylthio group", use is made of a $C_{6-10}$arylthio group optionally substituted with 1 to 3 substituents selected from, for example, halogen, nitro, $C_{1-6}$alkyl and $C_{1-6}$alkoxy. More specifically, for example, o-nitrophenylthio is used.

"Substituted silyl group" forms, together with the amino group to be protected, a group of the formula $R^6R^7R^8SiNH—$, $(R^6R^7R^8Si)_2N—$ or the formula:

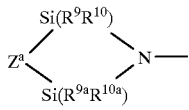

wherein $R^6$, $R^7$, $R^8$, $R^9$, $R^{10}$, $R^{9a}$ and $R^{10a}$ each is a $C_{1-6}$alkyl group or a $C_{6-10}$aryl group, and $Z^a$ is a $C_{1-3}$alkylene group, e.g. methylene, ethylene and propylene.

Preferable examples of "substituted silyl group" include trimethylsilyl, tert-butyl dimethylsilyl and $—Si(CH_3)_2CH_2CH_2Si(CH_3)_2—$.

As "2-$C_{1-10}$alkoxy-carbonyl-1-methyl-1-ethenyl group", use is made of, specifically, for example, 2-methoxycarbonyl-1-methyl-1-ethenyl, 2-ethoxycarbonyl-1-methyl-1-ethenyl, 2-tert-butoxycarbonyl-1-methyl-1-ethenyl, 2-cyclohexyloxycarbonyl-1-methyl-1-ethenyl and 2-norbornyloxycarbonyl-1-methyl-1-methyl-1-ethenyl.

Preferable examples of "alkali metal" shown by M' include sodium and potassium, the former being especially preferable.

$R^1$ is preferably amino group, when the anitbacterial activity is taken into consideration.

$R^2$ is a lower alkyl group substituted with fluorine. As the "lower alkyl group substituted with fluorine, use is made of, for example, fluoromethyl, 2-fluoroethyl, 1,2-difluoroethyl and 2,2,2-trifluoroethyl, preferably a $C_{1-6}$alkyl group substituted with 1 to 3 fluorine, such as fluoromethyl and 2-fluoroethyl, more preferably fluoromethyl.

Examples of "optionally substituted hydrocarbon group" shown by $R^3$ include an optionally substituted alkyl group, an optionally substituted alkenyl group, an optionally substituted alkynyl group, an optionally substituted aralkyl group and an optionally substituted cyclic hydrocarbon group. As the "alkyl group" of "optionally substituted alkyl group", a $C_{1-6}$alkyl, for example, is preferable, especially a $C_{1-3}$alkyl such as methyl, ethyl, isopropyl, etc. are preferable. As the "alkenyl group" of "optionally substituted alkenyl group", a $C_{2-6}$alkenyl group, for example, is preferable.

Preferable examples of the "alkynyl group" of "optionally substituted alkynyl group" include $C_{2-6}$alkynyl groups. Preferable examples of the "aralkyl group" of "optionally substituted aralkyl group" include $C_{7-19}$aralkyl groups. Preferable examples of the "cyclic hydrocarbon group" of "optionally substituted cyclic hydrocarbon group" include 3- to 7-membered non-aromatic cyclic hydrocarbon groups such as cyclopropyl, cyclobutyl, cyclopentyl, cyclohexyl, cycloheptyl, 2-cyclopenten-1-yl, 3-cyclopenten-1-yl, 2-cyclohexen-1-yl and 3-cyclohexen-1-yl and $C_{6-10}$aryl group such as phenyl, naphtyl, etc.

Examples of the substituents, which the above-mentioned "hydrocarbon group" may optionally have, include heterocyclic groups, hydroxyl group, $C_{3-10}$cycloalkyl groups, $C_{1-6}$alkoxy groups, $C_{3-7}$cycloalkyloxy groups, $C_{6-10}$aryloxy groups, $C_{7-19}$aralkyloxy groups, heterocyclic-oxy groups, mercapto group, $C_{1-6}$alkylthio groups, $C_{3-10}$cycloalkylthio groups, $C_{6-10}$arylthio groups, $C_{7-19}$aralkylthio groups, heterocyclic thio groups, amino group, mono-$C_{1-6}$alkylamino groups, di-$C_{1-6}$alkylamino groups, tri-$C_{1-6}$alkyl ammonium groups, $C_{3-10}$cycloalkylamino groups, $C_{6-10}$arylamino groups, $C_{7-19}$aralkylamino groups, heterocyclic amino groups, cyclic amino groups, azido group, nitro group, halogen atoms, cyano group, carboxyl group, $C_{1-10}$alkoxy-carbonyl groups, $C_{1-10}$aryloxy-carbonyl groups, $C_{7-19}$aralkyloxy-carbonyl groups, $C_{6-10}$aryl-carbonyl groups, $C_{1-6}$alkanoyl groups, $C_{3-5}$alkenoyl groups, $C_{6-10}$aryl-carbonyloxy groups, $C_{2-6}$alkanoyloxy groups, $C_{3-5}$alkenoyloxy groups, optionally substituted carbamoyl groups, optionally substituted thiocarbamoyl groups, optionally substituted carbamoyloxy groups, phthalimido group, $C_{1-6}$alkanoylamino groups, $C_{6-10}$aryl-carbonylamino groups, $C_{1-10}$alkoxy-carboxamido groups, $C_{6-10}$aryloxy-carboxamido groups and $C_{7-19}$aralkyloxy-carboxamido groups. The number of these substituents, which may be the same as or different from one another, ranges from 1 to 4. Among specific examples of the substituent of the above-mentioned "hydrocarbon group", as "optionally substituted carbamoyl group, use is made of, for example, carbamoyl groups and cyclic aminocarbonyl groups optionally substituted with one or two substituents selected from, for example, $C_{1-6}$alkyl groups, $C_{1-6}$alkanoyl groups, $C_{6-10}$arylcarbonyl groups and $C_{1-6}$alkoxy-phenyl groups. More specifically, use is made of, for example, carbamoyl, N-methylcarbamoyl, N-ethylcarbamoyl, N,N-dimethylcarbamoyl, N,N-diethylcarbamoyl, N-phenylcarbamoyl, N-acetylcarbamoyl, N-benzoylcarbamoyl, N-(p-methoxyphenyl)carbamoyl, pyrrolidinocarbonyl, piperidinocarbonyl, piperazinocarbonyl and morpholinocarbonyl. As "optionally substituted thiocarbamoyl groups", use is made of thiocarbamoyl groups optionally substituted with one or two substituents selected from, for example, $C_{1-6}$alkyl groups and $C_{6-10}$aryl groups, which are exemplified by thiocarbamoyl, N-methyl thiocarbamoyl and N-phenyl thiocarbamoyl. As "optionally substituted carbamoyloxy groups", use is made of carbamoyloxy groups optionally substituted with one or two substituents selected from, for example, $C_{1-6}$alkyl groups and $C_{6-10}$aryl groups. Specific examples of them include carbamoyloxy, N-methyl carbamoyloxy, N,N-dimethyl carbamoyloxy, N-ethyl carbamoyloxy and N-phenyl carbamoyloxy.

As heterocyclic groups and heterocyclic groups in heterocyclic oxy groups, heterocyclic thio groups and heterocyclic amino groups in the substituents of "hydrocarbon groups", use is made of groups similar to those in the "heterocyclic carbonyl groups" as mentioned as "protective group" in an optionally protected amino group $R^1$.

As substituents which "alkyl groups" of "optionally substituted alkyl groups", "alkenyl groups" of "optionally substituted alkenyl groups", "alkynyl group" of "optionally substituted alkynyl group", "aralkyl groups" of "optionally substituted aralkyl groups" and "cyclic hydrocarbon groups" of "optionally substituted cyclic hydrocarbon groups may optionally have, use is made of, for example, those similar to the substituents which "hydrocarbon groups" of the above-mentioned "optionally substituted hydrocarbon groups" may optionally have.

More preferable examples of "optionally substituted hydrocarbon group" shown by $R^3$ include $C_{1-6}$alkyl groups optionally substituted with one to three substituents selected from, for example, hydroxyl group, $C_{3-10}$cycloalkyl groups, $C_{1-6}$alkoxy groups, $C_{1-6}$alkylthio groups, amino group, halogen atoms, carboxyl group, $C_{1-10}$alkoxycarbonyl groups, optionally substituted carbamoyl group, cyano group, azido group and heterocyclic groups, which are more specifically exemplified by cyclopropylmethyl, methoxymethyl, ethoxymethyl, 1-methoxyethyl, 2-methoxyethyl, 1-ethoxyethyl, 2-hydroxyethyl, methylthiomethyl, 2-aminoethyl, 2-fluoroethyl, 2,2-difluoroethyl, chloromethyl, 2-chloroethyl, 2,2-dichloroethyl, 2,2,2-trichloroethyl, 2-bromoethyl, 2-iodoethyl, 2,2,2-trifluoroethyl, carboxymethyl, 1-carboxyethyl, 2-carboxyethyl, 2-carboxypropyl, 3-carboxypropyl, 1-carboxybutyl, cyanomethyl, 1-carboxy-1-methylethyl, methoxycarbonylmethyl, ethoxycarbonylmethyl, tert-butoxycarbonylmethyl, 1-methoxycarbonyl-1-methylethyl, 1-ethoxycarbonyl-1-methylethyl, 1-tert-butoxycarbonyl-1-methylethyl, 1-benzyloxycarbonyl-1-methylethyl, 1-pivaloyloxycarbonyl-1-methylethyl, carbamoylmethyl, N-methylcarbamoylmethyl, N,N-dimethylcarbamoylmethyl, 2-azidoethyl, 2-(pyrazolyl)ethyl, 2-(imidazolyl)ethyl, 2-(2-oxopyrrolidin-3-yl)ethyl and 1-carboxyl-1-(2,3,4-trihydroxyphenyl)methyl. Most preferable examples of "optionally substituted hydrocarbon group" include straight-chain and branched $C_{1-3}$alkyl groups such as methyl, ethyl, n-propyl and isopropyl, and straight-chain $C_{1-6}$alkyl groups optionally substituted with 1 to 3 substituents selected from halogen, hydroxyl group, $C_{1-6}$alkoxy group, carboxyl group, $C_{1-10}$alkoxycarbonyl group, cyano group and carbamoyl group, which are exemplified by 2-fluoroethyl, 2-chloroethyl, 2-hydroxyethyl, 2-methoxyethyl, cyanomethyl, carboxymethyl, methoxycarbonylmethyl, ethoxycarbonylmethyl, carbamoylmethyl, N-methylcarbamoylmethyl and N,N-dimethylcarbamoylmethyl. Especially, $C_{1-3}$alkyl groups (e.g. methyl and ethyl) are preferable.

The ring A may optionally have, at any possible position, preferably, one or two substituents. Examples of these substituents include hydroxyl group, hydroxy $C_{1-6}$alkyl group, $C_{1-6}$alkyl group, $C_{2-6}$alkenyl group, $C_{2-6}$alkynyl group, $C_{3-10}$cycloalkyl group, $C_{5-6}$cycloalkenyl group, $C_{3-10}$cycloalkyl-$C_{1-6}$alkyl group, $C_{6-10}$aryl group, $C_{7-12}$aralkyl group, heterocyclic group, $C_{1-6}$alkoxy group, $C_{1-6}$alkoxy-$C_{1-6}$alkyl group, amino-$C_{1-6}$alkoxy group, $C_{3-10}$cycloalkyloxy group, $C_{6-10}$aryloxy group, $C_{7-19}$aralkyloxy group, mercapto group, mercapto-$C_{1-6}$alkyl group, sulfo group, sulfo-$C_{1-6}$alkyl group, $C_{1-6}$alkylthio group, $C_{1-6}$alkylthio $C_{1-6}$alkyl group, $C_{3-10}$cycloalkylthio group, $C_{6-10}$arylthio group, $C_{7-19}$aralkylthio group, amino-$C_{1-6}$alkylthio group, amino group, amino-$C_{1-6}$alkyl group, mono-$C_{1-6}$alkylamino group, di-$C_{1-6}$alkylamino group, mono-$C_{1-6}$alkylamino-$C_{1-6}$alkyl group, di-$C_{1-6}$alkylamino-$C_{1-6}$ alkyl group, $C_{3-10}$cycloalkylamino group, $C_{6-10}$arylamino group, $C_{7-19}$aralkylamino group, cyclic amino group, cyclic amino-$C_{1-6}$alkyl group, cyclic amino-$C_{1-6}$alkylamino group, acylamino group, ureido group, $C_{1-6}$alkylureido group, azido group, nitro group, halogen atom, halogeno-$C_{1-6}$alkyl group, cyano group, cyano-$C_{1-6}$alkyl group, carboxyl group, carboxy-$C_{1-6}$alkyl group, $C_{1-10}$alkoxy-carbonyl group, $C_{1-10}$alkoxy-carbonyl-$C_{1-6}$alkyl group, $C_{6-10}$aryloxy-carbonyl group, $C_{7-19}$aralkyloxy-carbonyl group, $C_{6-10}$aryl-$C_{1-6}$alkanoyl group, $C_{16}$alkanoyl group, $C_{2-6}$alkanoyl-$C_{1-6}$alkyl group, $C_{3-5}$alkenoyl group, $C_{6-10}$aryl-$C_{1-6}$alkanoyloxy group, $C_{2-6}$alkanoyloxy group, $C_{2-6}$alkanoyloxy-$C_{1-6}$alkyl group, $C_{3-5}$alkenoyloxy group, carbamoyl-$C_{1-6}$alkyl group, carbamoyl group, thiocarbamoyl group, carbamoyloxy group, carbamoyloxy-$C_{1-6}$alkyl group, $C_{1-6}$alkanoylamino group, $C_{6-10}$aryl-$C_{1-6}$alkanoylamino group, sulfonamido group, carboxamido group, $C_{1-10}$alkoxy-carboxamido group, $C_{6-10}$aryloxy-carboxamido group and $C_{7-19}$aralkyloxy-carboxamido group.

As the acyl group of "acylamino group" in the substituent on the above-mentioned pyridine ring, use is made of, for example, $C_{1-6}$alkanoyl group, $C_{3-5}$alkenoyl group, $C_{3-10}$cycloalkyl-carbonyl group, $C_{5-6}$cycloalkenyl-carbonyl group, $C_{6-10}$aryl-carbonyl group, $C_{7-19}$ aralkyl-carbonyl group, amino acid residue (acyl group formed by removing hydroxyl group of carboxyl group of amino acid, as specifically exemplified by glycyl, sarcosyl, alanyl, valyl, leucyl, isoleucyl, seryl, threonyl, cysteinyl, cystinyl, methionyl, asparagyl, glutamyl, lysyl, arginyl, phenylglycyl, phenylalanyl, tyrosyl, histidyl, tryptophanyl and prolyl), amino $C_{1-6}$ alkyl-carbonyl group, mono-$C_{1-6}$alkylamino-$C_{1-6}$alkyl-carbonyl group, di-$C_{1-6}$alkylamino-$C_{1-6}$alkyl-carbonyl group and cyclic aminoalkylcarbonyl group.

As "heterocyclic group" in the substituent on the above-mentioned pyridine ring, use is made of ones similar to "heterocyclic group" in the above-mentioned "heterocyclic carbonyl group" mentioned as a protective group of "optionally protected amino group $R^1$.

Among the compound [I], the compounds (I-a], their esters or salts are preferable, and the compounds of the formula:

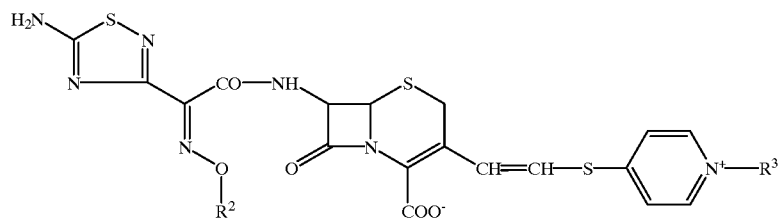

[I-b]

wherein symbols are of the same meaning as defined above, or their esters or salts are more preferable.

Most preferable compounds of the formula [I-a] are those wherein $R^2$ is a lower alkyl group substituted with fluorine and $R^3$ is a $C_{1-6}$alkyl group (e.g. methyl, ethyl, propyl and isopropyl).

In the above-mentioned compound [I], the mark $\ominus$ attached on the right shoulder of —COO at the 4-position shows that the carboxyl group forms carboxylate anion, making a pair with the positive charge on the pyridine ring (hereinafter sometimes simply referred to as $A^\oplus$). On the other hand, the compound [I] may optionally form a pharmaceutically acceptable ester or salt. As the pharmaceutically acceptable salt, use is made of, for example, inorganic basic salts, ammonium salts, organic basic salts, inorganic acid addition salts, organic acid addition salts and basic amino acid salts. As the inorganic base capable of forming an inorganic basic salt, use is made of, for example, alkali metal (e.g. sodium and potassium) and alkaline earth metals (e.g. calcium); as the organic base capable of forming an organic basic salt, use is made of, for example, procaine, 2-phenylethyl benzylamine, dibenzylethylenediamine, ethanolamine, diethanolamine, trishydroxymethylaminomethane, polyhydroxyalkylamine and N-methylglucosamine; as an inorganic acid capable of forming an inorganic acid addition salt, use is made of, for example, hydrochloric acid, hydrobromic acid, sulfuric acid, nitric acid and phosphoric acid; as an organic acid capable of forming an organic acid addition salt, use is made of, for example, p-toluenesulfonic acid, methanesulfonic acid, formic acid, trifluoroacetic acid and maleic acid; and, as a basic amino acid capable of forming a basic amino acid salt, use is made of, for example, lysine, arginine, ornithine and histidine. Among these salts, basic salts (i.e. inorganic basic salts, ammonium salts, organic basic salts and basic amino acid salts) mean those capable of being formed in the case where an acid group such as carboxyl group and sulfo group exists in the substituents $R^1$, $R^2$, $R^3$ or $A^\oplus$ of the compound [I] or where carboxyl group exists at the 4-position; and acid addition salts (i.e. inorganic acid addition salts and organic acid addition salts) mean those capable of being formed in the case where a basic group such as amino group, monoalkylamino group, dialkylamino group, cycloalkylamino group, arylamino group, aralkylamino group, cyclic amino group and N-containing heterocyclic group exists in the substituent $R^1$, $R^2$, $R^3$ or $A^\ominus$ of the compound [I]. And, the acid addition salts include salts in which one mol. of acid is added to the moiety forming the internal salt of the compound [I], i.e. the carboxylate moiety ($COO^\ominus$) at the 4-position and CH=CH—$A^\oplus$ moiety at the 3-position to form a salt in which the 4-position is carboxyl group (COOH) and the 3-position of CH=CH—$A^\oplus.Y^\ominus$ wherein $Y^\ominus$ stands for anion formed by removing proton $H^\oplus$ from inorganic acid or organic acid, the anion being exemplified by chloride ion, bromide ion, sulfate ion, p-toluenesulfonate ion, methanesulfonate ion and trifluoroacetate ion]. Ester derivatives of the compound [I] mean esters producible by esterifying the carboxyl group in the molecule which are utilizable as intermediate of the synthesis and are metabolically unstable and non-toxic esters. Examples of the ester utilizable as intermediate of the synthesis include optionally substituted $C_{1-6}$alkyl ester, $C_{2-6}$alkenyl ester, $C_{3-10}$cycloalkyl ester, $C_{3-10}$cycloalkyl $C_{1-6}$alkyl ester, optionally substituted $C_{6-10}$aryl ester, optionally substituted $C_{7-12}$aralkyl ester, di-$C_{6-10}$aryl-methyl ester, tri-$C_{6-10}$aryl-methyl ester and substituted silyl ester.

As "optionally substituted $C_{1-6}$alkyl ester", use is made of, for example, methyl, ethyl, n-propyl, isopropyl, n-butyl, isobutyl, sec-butyl, tert-butyl, n-pentyl and n-hexyl, which may be substituted with one to three of, for example, benzyloxy, $C_{1-4}$alkyl sulfonyl (e.g. methyl sulfonyl), trimethyl silyl, halogen (e.g. fluorine, chlorine and bromine), acetyl, nitrobenzoyl, mesylbenzoyl, phthalimido, succinimide, benzenesulfonyl, phenylthio, di-$C_{1-4}$alkylamino (e.g. dimethylamino), pyridyl, $C_{1-4}$alkyl sulfinyl (e.g. methyl sulfinyl) and cyano. Examples of such groups include benzyloxymethyl, 2-methylsulfonylethyl, 2-trimethylsilylethyl, 2,2,2-trichloroethyl, 2-iodoethyl, acetylmethyl, p-nitrobenzoylmethyl, p-mesylbenzoylmethyl, phthalimidomethyl, succinimidomethyl, benzenesulfonylmethyl, phenylthiomethyl, dimethylaminoethyl, pyridine-oxido-2-methyl, methylsulfinylmethyl and 2-cyano-1,1-dimethylethyl.

As the $C_{2-6}$alkenyl group forming "$C_{2-6}$alkenyl ester", use is made of, for example, vinyl, allyl, 1-propenyl, isopropenyl, 1-butenyl, 2-butenyl, 3-butenyl, methallyl, 1,1-dimethylallyl and 3-methyl-3-butenyl.

As the $C_{3-10}$cycloalkyl group forming "$C_{3-10}$cycloalkyl ester", use is made of, for example, cyclopropyl, cyclobutyl, cyclopentyl, cyclohexyl, cycloheptyl, norbornyl and adamantyl.

As the $C_{3-10}$cycloalkyl-$C_{1-6}$alkyl group forming "$C_{3-10}$cycloalkyl-$C_{1-6}$alkyl ester", use is made of, for example, cyclopropylmethyl, cyclopentylmethyl and cyclohexylmethyl.

As "$C_{6-10}$aryl group" forming "optionally substituted $C_{6-10}$aryl ester", use is made of, for example, phenyl, α-naphthyl, β-naphthyl and biphenylyl, which may optionally be substituted with one to three of, for example, nitro and halogen (e.g. fluorine, chlorine and bromine). Such groups as above are specifically exemplified by p-nitrophenyl and p-chlorophenyl.

As "$C_{7-12}$aralkyl group" forming "optionally substituted $C_{7-12}$aralkyl ester", use is made of, for example, benzyl, 1-phenylethyl, 2-phenylethyl, phenylpropyl and naphthylmethyl, which may optionally be substituted with one to three of, for example nitro, $C_{1-4}$alkoxy (e.g. methoxy), $C_{1-4}$alkyl (e.g. methyl and ethyl) and hydroxy. Specific examples of such groups include p-nitrobenzyl, p-methoxybenzyl and 3,5-di-tert-butyl-4-hydroxybenzyl.

As the di-$C_{6-10}$aryl-methyl group forming "di-$C_{6-10}$aryl-methyl ester", use is made of, among others, benzhydryl; as the tri-$C_{6-10}$aryl-methyl group forming tri $C_{6-10}$aryl-methyl ester, use is made of, among others, trityl; as the substituted silyl group forming substituted silyl ester, use is made of, for example, trimethylsilyl, tert-butyl dimethylsilyl and —Si(CH$_3$)$_2$CH$_2$CH$_2$Si(CH$_3$)$_2$—. The above-mentioned esters include ester at 4-position. The compound, wherein the 4-position is the above-mentioned ester group, forms a salt in which the 3-position is CH=CH—S—$A^\oplus Y^\ominus$ [wherein symbols are of the same meaning as defined above].

The present invention includes, besides the above-described ester derivatives, pharmacologically acceptable compounds convertible into the compound [I] in a living body.

In the case where $A^{61}$ has amino group as the substituent, the amino group may optionally be substituted. As substituents on the amino group, use is made of, for example, protective groups of the optionally protected amino groups shown by $R^1$.

The compound [I] and starting compounds of this invention include cis-isomer (Z-compound), trans-isomer (E-compound) and a cis-trans mixture. The compound [I] of this invention is preferably a trans-isomer (E-compound).

Referring to the compound [I], the cis-isomer (Z-compound), for example, means one of the geometrical isomers having the partial structure represented by the formula [VII], and the trans-isomer means a geometrical isomer having the partial structure of the formula [VIII].

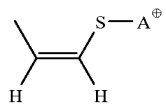

[VII]

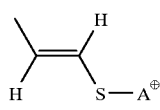

[VIII]

In the present specification, specific examples of the respective substituents are, unless specifically described, as follows.

halogen: fluoro, chloro, bromo and iodo;

$C_{1-6}$alkyl group: methyl, ethyl, propyl, isopropyl, butyl, isobutyl, t-butyl, pentyl, 2,2-dimethylpropyl and hexyl;

$C_{2-6}$alkenyl group: vinyl, allyl, 1-propenyl, isopropenyl, 1-butenyl, 2-butenyl, 3-butenyl, methallyl and 1,1-dimethylallyl;

$C_{2-6}$alkynyl group: ethynyl, 1-propynyl, 2-propynyl, 2-butynyl, 2-pentynyl and 2-hexynyl;

$C_{3-10}$cycloalkyl group: cyclopropyl, cyclobutyl, cyclopentyl, cyclohexyl, cycloheptyl, cyclooctyl and cyclodecyl;

$C_{5-6}$cycloalkenyl group: cyclopentenyl, cyclopentadienyl, cyclohexenyl and cyclohexadienyl;

$C_{6-10}$aryl group: phenyl and napthyl;

$C_{7-20}$aralkyl group: benzyl, 1-phenylethyl, 2-phenylethyl, phenylpropyl, naphthylmethyl and benzhydryl;

halogeno-$C_{1-6}$alkyl group: fluoromethyl, difluoromethyl, trifluoromethyl, chloromethyl, dichloromethyl, trichloromethyl, 2-fluoroethyl 2,2-difluoroethyl, 2,2,2-trifluoroethyl, 2-chloroethyl, 2,2-dichloroethyl, 2,2,2-trichloroethyl 2-bromoethyl and 2-iodoethyl;

cyano-$C_{1-6}$alkyl group: cyanomethyl and 2-cyanoethyl;

carboxy-$C_{1-6}$alkyl group: carboxymethyl, 1-carboxyethyl and 2-carboxyethyl;

sulfo-$C_{1-6}$alkyl group: sulfomethyl and 2-sulfoethyl;

hydroxy-$C_{1-6}$alkyl group: hydroxymethyl, 1-hydroxyethyl, 2-hydroxyethyl and 3-hydroxyethyl;

mercapto-$C_{1-6}$alkyl group: mercaptomethyl, 1-mercaptoethyl and 2-mercaptoethyl; amino-$C_{1-6}$alkyl group: aminomethyl, 2-aminoethyl and 3-aminopropyl;

mono-$C_{1-6}$alkylamino-$C_{1-6}$alkyl group: methylaminomethyl, ethylaminomethyl, 2-(N-methylamino)ethyl, and 3-(N-methylamino)propyl;

di-$C_{1-6}$alkylamino-$C_{1-6}$alkyl group: N,N-dimethylaminomethyl, N,N-diethylaminomethyl, 2-(N,N-dimethylamino)ethyl, 2-(N,N-diethylamino)ethyl and 3-(N,N-dimethylamino)propyl;

cyclic amino-$C_{1-6}$alkyl group: pyrrolidinomethyl, piperidinomethyl, piperazinomethyl, morpholinomethyl and 2-(morpholino)ethyl;

$C_{1-6}$alkoxy-$C_{1-6}$alkyl group: methoxymethyl, ethoxymethyl and 2-methoxyethyl;

$C_{1-6}$alkylthio-$C_{1-6}$alkyl group: methylthiomethyl and 2-methylthioethyl;

$C_{3-10}$cycloalkyl-$C_{1-6}$alkyl group: cyclopropylmethyl, cyclobutylmethyl, cyclopentylmethyl, cyclohexylmethyl, cycloheptylmethyl, cyclooctylmethyl and cyclodecylmethyl;

$C_{2-6}$alkanoyl-$C_{1-6}$alkyl group: acetylmethyl, 1-acetylethyl and 2-acetylethyl;

$C_{2-6}$alkanoyloxy-$C_{1-6}$alkyl group: acetoxymethyl, 1-acetoxyethyl and 2-acetoxyethyl;

$C_{1-10}$alkoxy-carbonyl-$C_{1-6}$alkyl group: methoxycarbonylmethyl, ethoxycarbonylmethyl and tert-butoxycarbonylmethyl;

carbamoyl-$C_{1-6}$alkyl group: carbamoylmethyl and 2-carbamoylethyl;

carbamoyloxy-$C_{1-6}$alkyl group: carbamoyloxymethyl and 1-carbamoyloxyethyl;

$C_{1-6}$alkxoy group: methoxy, ethoxy, propoxy, isopropoxy, butoxy, isobutoxy, t-butoxy, pentyloxy, 2,2-dimethylpropyloxy and hexyloxy;

$C_{3-10}$cycloalkyloxy group: cyclopropyloxy, cyclobutyloxy, cyclopentyloxy, cyclohexyloxy, cycloheptyloxy, cyclooctyloxy and cyclodecyloxy;

$C_{6-10}$aryloxy group: phenoxy and naphthyloxy;

$C_{7-19}$aralkyloxy group: benzyloxy, 1-phenylethyloxy, 2-phenylethyloxy and benzhydryloxy;

amino-$C_{1-6}$alkoxy group: aminomethoxy, 2-aminoethoxy and 3-aminopropoxy;

$C_{1-6}$alkylthio group: methylthio, ethylthio, propylthio, butylthio, isobutylthio, t-butylthio, pentylthio, 2,2-dimethylpropylthio and hexylthio;

$C_{3-10}$cycloalkylthio group: cyclopropylthio, cyclobutylthio, cyclopentylthio, cyclohexylthio, cycloheptylthio, cyclooctylthio and cyclodecylthio;

$C_{6-10}$arylthio group: phenylthio and naphthylthio;

$C_{7-19}$aralkylthio group: benzylthio, phenylethylthio, benzhydrylthio and tritylthio;

amino-$C_{1-6}$alkylthio group: aminomethylthio, 2-aminoethylthio and 3-aminopropylthio;

$C_{1-6}$alkylsulfonyl group: methylsulfonyl, ethylsulfonyl, propylsulfonyl, isopropylsulfonyl, butylsulfonyl, isobutylsulfonyl, t-butylsulfonyl, pentylsulfonyl, 2,2-dimethylpropylsulfonyl and hexylsulfonyl;

mono-$C_{1-6}$alkylamino group: methylamino, ethylamino, n-propylamino and n-butylamino;

di-$C_{1-6}$alkylamino group: dimethylamino, diethylamino, methylethylamino, di-(n-propyl)amino and di-(n-butyl)amino;

tri-$C_{1-6}$alkylammonium group: trimethylammonium;

$C_{3-10}$cycloalkylamino group: cyclopropylamino, cyclopentylamino and cyclohexylamino;

$C_{6-10}$arylamino group: anilino and N-methylanilino;

$C_{7-19}$aralkylamino group: benzylamino, 1-phenylethylamino, 2-phenylethylamino and benzhydrylamino;

cyclic amino group: pyrrolidino, piperidino, piperazino, morpholino and 1-pyrrolyl;

cyclic amino-$C_{1-6}$alkylamino group: pyrrolidinoethylamino, piperidinoethylamino, piperazinoethylamino and morpholinoethylamino;

$C_{1-6}$alkanoylamino group: acetamido, propionamido, butyroamido, valeroamido and pivaloamido;

$C_{6-10}$aryl-carbonylamino group; benzamido, naphthoylamido and phthalimido;

$C_{6-10}$aryl-$C_{1-6}$alkanoylamino group: phenylacetylamino;

$C_{1-6}$alkanoyl group: formyl, acetyl propionyl, butyryl, valeryl, pivaloyl, succinyl and glutaryl;

$C_{2-6}$alkanoyloxy group: acetoxy, propionyloxy, butyryloxy, valeryloxy and pivaloyloxy;

$C_{3-5}$alkenoyl group: acryloyl, crotonoyl and maleoyl;

$C_{3-5}$alkenoyloxy group: acryloyloxy, crotonoyloxy and maleoyloxy;

$C_{6-10}$aryl-carbonyl group: benzoyl, naphthoyl and phthaloyl;

$C_{6-10}$aryl-carbonyloxy group: benzoyloxy and naphthoyloxy;

$C_{3-10}$cycloalkyl-carbonyl group: cyclopropylcarbonyl, cyclobutylcarbonyl, cyclopentylcarbonyl, cyclohexylcarbonyl, cycloheptylcarbonyl, cyclooctylcarbonyl and cyclodecylcarbonyl;

$C_{5-6}$cycloalkenyl-carbonyl group: cyclopentenylcarbonyl, cyclopendadienylcarbonyl, cyclohexenylcarbonyl and cyclohexadienyl;

$C_{7-9}$aralkyl-carbonyl group: phenylacetyl, phenylpropionyl, α,α-diphenylacetyl and α,α,α-triphenylacetyl;

$C_{6-10}$aryl-$C_{1-6}$alkanoyl group: phenylacetyl;

$C_{6-10}$aryl-$C_{1-6}$alkanoyloxy group: phenylacetyloxy;

$C_{1-10}$alkoxy-carbonyl group: methoxycarbonyl, ethoxycarbonyl, propoxycarbonyl, isopropoxycarbonyl, butoxycarbonyl, isobutoxycarbonyl, t-butoxycarbonyl, pentyloxycarbonyl, 2,2-dimethylpropyloxycarbonyl, hexyloxycarbonyl, heptyloxycarbonyl and decyloxycarbonyl;

$C_{1-10}$alkoxy-carbonyloxy group: methoxycarbonyloxy, ethoxycarbonyloxy, propoxycarbonyloxy, isopropoxycarbonyloxy, butoxycarbonyloxy, isobutoxycarbonyloxy, t-butoxycarbonyloxy, pentyloxycarbonyloxy, 2,2-dimethylpropyloxycarbonyloxy, hexyloxycarbonyloxy, heptyloxycarbonyloxy and decyloxycarbonyloxy;

$C_{3-10}$cycloalkyloxy-carbonyl group: cyclopropyloxycarbonyl, cyclobutyloxycarbonyl, cyclopentyloxycarbonyl, cyclohexyloxycarbonyl, cycloheptyloxycarbonyl, cyclooctyloxycarbonyl and cyclodecyloxycarbonyl;

$C_{3-10}$cycloalkyloxy-carbonyloxy group: cyclopropyloxycarbonyloxy, cyclohexyloxycarbonyloxy, cycloheptyloxycarbonyloxy, cyclooctyloxycarbonyloxy and cyclodecyloxycarbonyloxy;

$C_{5-10}$cross-linked cyclic hydrocarbon oxy-carbonyl group: norbornyloxycarbonyl and adamantyloxycarbonyl: $C_{2-10}$alkenyloxy-carbonyl group: allyloxycarbonyl;

$C_{6-10}$aryloxy-carbonyl group: phenoxycarbonyl, naphthyloxycarbonyl;

$C_{7-19}$aralkyloxy-carbonyl group: benzyloxycarbonyl and benzhydryloxycarbonyl; amino-$C_{1-6}$alkyl-carbonyl group: 2-aminoethylcarbonyl and 3-aminopropylcarbonyl;

mono-$C_{1-6}$alkylamino-$C_{1-6}$alkyl-carbonyl group: methylaminomethylcarbonyl and 2-ethylaminoethylcarbonyl;

di-$C_{1-6}$alkylamino-$C_{1-6}$alkyl-carbonyl group: dimethylaminomethylcarbonyl and diethylaminomethylcarbonyl;

cyclic aminoalkylcarbonyl group: imidazolinomethyl and pyrazolinoethyl;

$C_{1-10}$alkoxy-carboxamido group: methoxycarboxamido ($CH_3OCONH$—), ethoxycarboxamido and tert-butoxycarboxamido;

$C_{6-10}$aryloxy-carboxamido group: phenoxycarboxamido ($C_6H_5OCONH$—);

$C_{7-10}$aralkyloxy-carboxamido group: benzyloxycarboxamido ($C_6H_5CH_2OCONH$—) and benzhydryloxycarboxamido;

$C_{1-6}$alkylureido group: methylureido, ethylureido and n-propylureido; and sulfonamido group: methanesulfonyl and ethanesulfonyl.

Methods of producing the compound [I] of this invention are hereinafter described in detail. Method (1): The compound [I] can be synthesized by allowing, for example, a 7-amino compound of the formula:

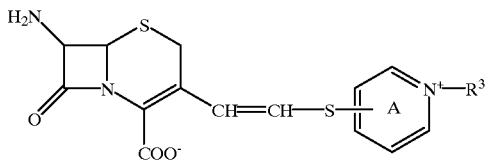

[II]

wherein symbols are of the same meaning as defined above, or an ester or salt thereof to react with carboxylic acid of the formula:

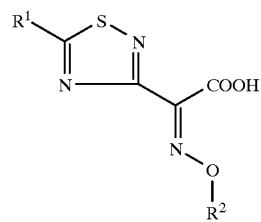

wherein symbols are of the same meaning as defined above (hereinafter referred to as $R^bOH$), or a salt or reactive derivative thereof.

This method comprises acylation of the 7-amino compound [II] with carboxylic acid $R^bOH$ or a salt or reactive derivative thereof. In this method, the carboxylic acid $R^bOH$ in the free state or in the form of a salt or reactive derivative thereof can be used as an agent for acylating the amino group at 7-position of the 7-amino compound [II]. More specifically, free acid $R^bOH$ or its reactive derivatives such as inorganic basic salts, organic basic salts, acid halides, acid azides, acid anhydrides, mixed acid anhydrides, active amides, active ester and active thioesters of the free acid $R^bOH$ are used for the acylation. Examples of inorganic basic salts include alkali metal salts (e.g. sodium salt and potassium salt) and alkaline earth metal salts (e.g. calcium salt); examples of organic basic salts include trimethylamine salt, triethylamine salt, tert-butyldimethylamine salt, dibenzylmethylamine salt, benzyldimethylamine salt, N,N-dimethylaniline salt, pyridine salt and quinoline salt; examples of acid halides include acid chloride and acid bromide; examples of mixed acid anhydrides include mono-$C_{1-6}$alkyl carbonate mixed acid anhydride (e.g. mixed acid anhydride of free acid $R^bOH$ with, for example, monomethyl carbonate, monoethyl carbonate, monoisopropyl carbonate, monoisobutyl carbonate, mono tert-butyl carbonate, monobenzyl carbonate, mono(p-nitrobenzyl) carbonate or monoallyl carbonate), $C_{1-6}$aliphatic carboxylic acid mixed anhydride (e.g. mixed acid anhydride of free acid $R^bOH$ with, for example, acetic acid, trichloroacetic acid, cyanoacetic acid, propionic acid, butyric acid, isobutyric acid, valeric acid, isovaleric acid, pivalic acid, trifluoroacetic acid, trichloroacetic acid or acetoacetic acid), $C_{7-12}$aromatic carboxylic acid mixed anhydride (e.g. mixed acid anhydride of free acid $R^bOH$ with, for example, benzoic acid, p-toluic acid or p-chlorobenzoic acid) and organic sulfonic acid mixed anhydride (e.g. mixed acid anhydride of free acid $R^bOH$ with, for example, methanesulfonic acid, ethanesulfonic acid, benzenesulfonic acid or p-toluenesulfonic acid); and examples of active amides include amide with an N-containing heterocyclic compound (e.g. acid amide of free acid $R^bOH$ with pyrazole, imidazole or benzotriazole, and these N-containing heterocyclic compounds may optionally be substituted with, for example, $C_{1-6}$alkyl group, $C_{1-6}$alkoxy group, halogen, oxo group, thioxo group, or $C_{1-6}$alkylthio group. As the active ester, any one usable for this purpose in the field of synthesizing β-lactam and peptide can be utilized, examples of which include, besides organic phosphoric acid ester (e.g. diethoxyphosphoric acid ester and diphenoxyphosphoric acid ester), p-nitrophenyl ester, 2,4-dinitrophenyl ester, cyanomethyl ester, pentachlorophenyl ester, N-hydroxysuccinimide ester, N-hydroxyphthalimide ester, 1-hydroxybenzotriazole ester, 6-chloro-1-hydroxybenzotriazole ester and 1-hydroxy-1H-2-pyridone ester. As the active thioester, mention is made of ester with an aromatic heterocyclic thiol compound [e.g.

2-pyridylthiol ester or 2-benzothiazolylthiol ester, and these heterocyclic ring may optionally be substituted with a $C_{1-6}$ alkyl group, a $C_{1-6}$ alkoxy group, halogen, or a $C_{1-6}$ alkylthio group]. On the other hand, the 7-amino compound [II] can be used in the free state, as a salt or ester thereof. Examples of salts of the 7-amino compound [II] include inorganic basic salts, ammonium salts, organic basic salts, inorganic acid-addition salts and organic acid addition salts. Examples of inorganic basic salts include alkali metal salts (e.g. sodium salt and potassium salt) and alkaline earth metal salts (e.g. calcium salt); examples of organic basic salts include trimethylamine salt, triethylamine salt, tert-butyldimethylamine salt, dibenzylmethylamine salt, benzyldimethylamine salt, N,N-dimethylaniline salt, pyridine salt and quinoline salt; examples of inorganic acid addition salts include hydrochloride, hydrobromide, sulfate, nitrate and phosphate; and examples of organic acid addition salts include formate, acetate, trifluoroacetate, methanesulfonate and p-toluenesulfonate. As the ester of 7-amino compound [II], mention is made of esters already described as the ester derivatives of compound [I], as exemplified by, more specifically, $C_{1-6}$alkyl ester, $C_{2-6}$alkenyl ester, $C_{3-10}$cycloalkyl ester, $C_{3-6}$cycloalkyl-$C_{1-6}$alkyl ester, $C_{6-10}$aryl ester, $C_{7-12}$aralkyl ester, di-$C_{6-10}$arylmethyl ester, tri-$C_{6-10}$arylmethyl ester and $C_{2-6}$alkanoyloxy-$C_{1-6}$alkyl ester. The starting compound $R^bOH$, its salts and reactive derivatives can readily be produced by known methods (e.g. methods disclosed in JPA S60(1985)-231684 or JPA S62 (1987)-149682) or methods analogous thereto. The reactive derivative of the compound $R^bOH$ can be allowed, after isolating from the reaction mixture, to react with the 7-amino compound [II], or the reaction mixture containing the reactive derivative of the compound $R^bOH$ can be allowed, as it is, to react with the 7-amino compound [II]. When carboxylic acid $R^bOH$ is used in the state of free acid or salt, a proper condensing agent is employed. As the condensing agent, use is made of N,N'-disubstituted carbodiimides such as N,N'-dicyclohexylcarbodiimide; azolides such as N,N'-carbonyldiimidazole and N,N'-thiocarbonyldiimidazole; a dehydrating agent such as N-ethoxycarbonyl-2-ethoxy-1,2-dihydroquinoline, phosphorus oxychloride and alkoxyacetylene; and 2-halogenopyridinium salts such as 2-chloropyridinium methyliodide and 2-fluoropyridinium methyliodide. When these condensing agents are used, the reaction is considered to proceed via a reactive derivative of carboxylic acid $R^bOH$. The reaction is conducted generally in a proper solvent which does not hamper the reaction. As the solvent, use is made of ethers such as dioxane, tetrahydrofuran, diethyl ether, tert-butyl methyl ether, diisopropyl ether and ethylene glycol-dimethyl ether; esters such as ethyl formate, ethyl acetate and n-butyl acetate; halogenated hydrocarbons such as dichloromethane, chloroform, carbon tetrachloride, trichlene and 1,2-dichloroethane; hydrocarbons such as n-hexane, benzene and toluene; amides such as formamide, N,N-dimethylformamide and N,N-dimethylacetamide; ketones such as acetone, methyl ethyl ketone and methyl isobutyl ketone; nitriles such as acetonitrile and propionitrile; and, besides, dimethyl sulfoxide, sulfolane, hexamethyl phosphoramide and water, for example, are employed singly or as a mixture solvent. The amount of an acylating agent ($R^bOH$) to be used ranges usually from about 1 to 5 mol., preferably from about 1 to 2 mol., relative to one mol. of the 7-amino compound [II]. The reaction is conducted at temperatures ranging from about −80 to 80° C., preferably from about −40 to 50° C., most preferably from about −30 to 30° C. The reaction time depends on the kinds of 7-amino compound [II] and carboxylic acid $R^bOH$, kinds of solvent (when a mixed solvent is employed, the mixing ratio as well) and reaction temperature, and ranges usually from about 1 minute to 72 hours, preferably from about 15 minutes to 3 hours. When acid halide is employed as the acylating agent, the reaction can be conducted in the presence of a deacidifier for the purpose of eliminating liberated hydrogen halogenide from the reaction mixture. Examples of the deacidifier include inorganic base such as sodium carbonate, potassium carbonate, calcium carbonate and sodium hydrogencarbonate; tertiary amine such as triethylamine, tri(n-propyl)amine, tri(n-butyl)amine, diisopropylethylamine, cyclohexyl dimethylamine, pyridine, lutidine, gamma-collidine, N,N-dimethyl aniline, N-methyl piperidine, N-methylpyrrolidine and N-methyl morpholine; and alkylene oxide such as propylene oxide and epichlorohydrin.

The starting 7-amino compound [II] of this reaction or an ester or salt thereof can be produced by, for example, the following steps: the compound of the formula:

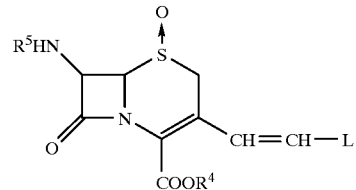

[IX]

[wherein $R^4$ is the protective group of carboxyl group and $R^5$ is the protecting group of amino group, L stands for a halogen atom, a lower acyloxy group or sulfonyloxy group and other symbols are of the same meaning as defined above] is allowed to react with an optionally substituted pyridine compound of the formula:

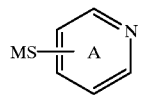

[IV]

wherein M is hydrogen or an alkali metal and the other symbols are of the same meaning as defined above, or a salt thereof to give a compound of the formula:

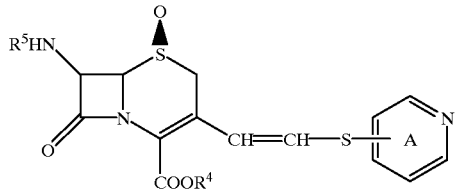

[X]

wherein symbols are of the same meaning as defined above, or a salt thereof, then, S-oxide is reduced by the method described in, for example, JPA S55(1980)-154978 to give the compound of the formula:

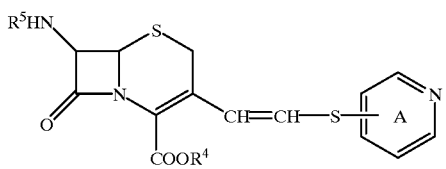

[XI]

wherein symbols are of the same meaning as defined above, or a salt thereof, followed by allowing the compound [XI] to react with a compound of the formula $R^3-X$ (X is a leaving group) to remove the protecting group from the compound of the formula:

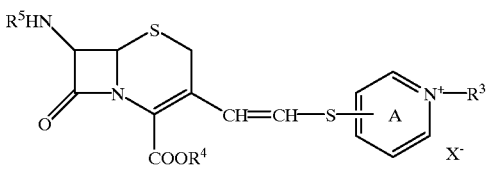

[XII]

wherein symbols are of the same meaning as defined above. As the carboxyl-protecting group shown by $R^4$, mention is made of the above-mentioned ester. Especially, readily removable carboxyl-protecting groups, which are conventionally employed in this field, such as tri(lower) alkyl silyl group e.g. trimethyl silyl group, benzhydryl group, p-methoxybenzyl group, tert-butyl group, p-nitrobenzyl group and phenacyl group, are preferable.

As the amino-protecting group shown by $R^5$, mention is made of the above-mentioned amino-protecting group of "optionally protected amino group $R^1$". Especially, tri (lower) alkyl silyl groups such as trimethyl silyl group; acyl type protecting groups such as formyl group, trifluoroacetyl group, acetyl group, tert-butoxycarbonyl group, methoxy acetyl group, benzyloxy carbonyl group and p-nitrobenzyloxy carbonyl group; and aralkyl type protecting group such as benzyl group, benzhydryl group and trityl group are preferable.

Preferable examples of X include halogen atoms such as chlorine, bromine and iodine; $C_{2-4}$acyloxy groups such as acetoxy, propionyloxy, butyryloxy and 3-oxobutyryloxy; $C_{1-10}$alkylsulfonyloxy groups such as methanesulfonyloxy, ethanesulfonyloxy and camphor sulfonyloxy; and $C_{6-10}$arylsulfonyloxy groups such as benzenesulfonyloxy, naphthalenesulfonyloxy, p-toluenesulfonyloxy, p-tert-butylbenzenesulfonyloxy, p-methoxybenzenesulfonyloxy, p-chlorobenzenesulfonyloxy and p-nitrobenzenesulfonyloxy. Especially, benzenesulfonyloxy and p-toluenesulfonyloxy groups are preferable.

X stands for a leaving group, which is preferably exemplified by halogen atom such as chlorine, bromine and iodine.

The pyridine compound [IV] is also used as a salt thereof. Examples of salts of the compound [IV] include alkali metal salts such as lithium salt, sodium salt and potassium salt; and addition salts with trialkylamine such as triethylamine and diisopropylamine.

The full nucleophilic substitution reaction between the compound [IX] and the compound [IV] is conducted, in general cases, preferably in an inactive solvent, as exemplified by ketones such as acetone; halogenated hydrocarbons such as chloroform, dichloromethane and dichloroethane; ethers such as diethyl ether, tetrahydrofuran and dioxane; nitriles such as acetonitrile; alcohols such as methanol, ethanol and n-propanol; amides such as dimethylformamide and dimethylacetamide; and sulfoxides such as dimethyl sulfoxide. The amount of the nucleophilic reagent [IV] to be used ranges usually from 1 to 5 mol., preferably from about 1 to 3 mol. relative to 1 mol. of the compound [IX]. The reaction temperature ranges from 0° C. to 100° C., preferably from 10° C. to 50° C. The reaction time ranges from 30 minutes to 24 hours, preferably from 1 to 10 hours. This reaction can be accelerated by the addition of a base or a salt. As the base and the salt, mention is made of, for example, inorganic bases such as sodium hydroxide, potassium hydroxide, sodium carbonate and potassium carbonate; and organic amine including trialkylamine such as triethylamine and and diisopropylethylamine. And, as the salt, use is made of, for example, quaternary ammonium salt such as tetrabutyl ammonium salt.

Examples of the compound represented by $R^3X$ to be reacted with the compound [X] include $C_{1-6}$ lower alkyl halide, $C_{2-6}$ lower alkenyl halide, $C_{2-6}$ lower alkynyl halide, hydroxy lower alkyl halide, carboxy lower alkyl halide, carbamoyl lower alkyl halide and lower alkenoyl lower alkyl halide. As the above-mentioned halides, mention is made of chloride, bromide and iodide. The reaction between the compound [X] and $R^3X$ is usually conducted preferably in an inactive solvent, for example, halogenated hydrocarbons such as dichloromethane, dichloroethane, chloroform and carbon tetrachloride; aromatic hydrocarbons such as benzene, toluene and xylene; ethers such as diethyl ether, tetrahydrofuran and dioxane; nitrites such as acetonitrile; alcohols such as methanol, ethanol and n-propanol; amides such as dimethylformamide and dimethylacetamide; and sulfoxides such as dimethyl sulfoxide. The amount of $R^3X$ to be employed ranges from 1 to 20 mol., preferably from 5 to 10 mol. The reaction temperature ranges from 15 to 100° C., preferably from 15 to 50° C. The reaction time ranges from 1 to 48 hours, preferably from 5 to 24 hours. The protective group of the compound [XI] obtained as above, when the protecting group is tri(lower)alkyl silyl group, can be removed by processing the compound with water. When the protective group is, for example, benzhydryl group, trityl group, p-methoxybenzyl group, tert-butyl group, tert-butoxycarbonyl group or formyl group, it can be removed by processing the compound with, for example, formic acid, hydrochloric acid, trifluoroacetic acid, phenol or cresol.

By the above-mentioned deprotection reaction, the 7-amino compound [II] can be obtained.

Method (2): A method of producing the compound described in (1) above, which comprises allowing, for example, a compound of the formula:

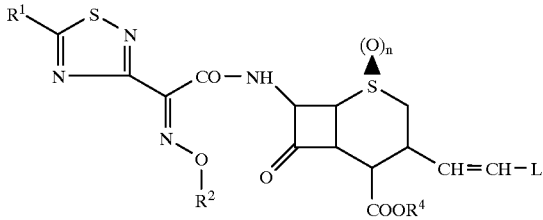

[III]

wherein n denotes 0 or 1, and other symbols are of the same meaning as defined above, to react with a pyridine compound of the formula:

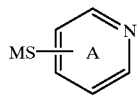

[IV]

wherein symbols are of the same meaning as defined above, to give a compound of the formula:

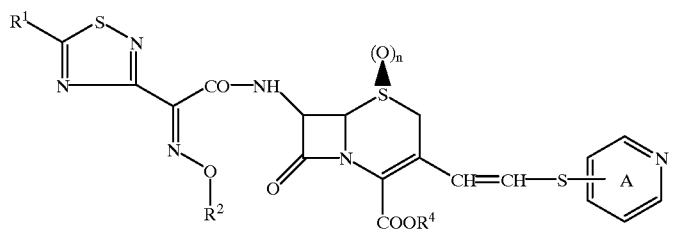

[V]

wherein each symbol is of the same meaning as defined above, which is then allowed to react with a compound of the formula $R^3X$ to give a compound of the formula:

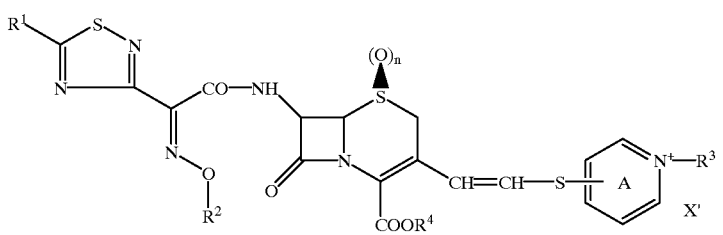

[VI]

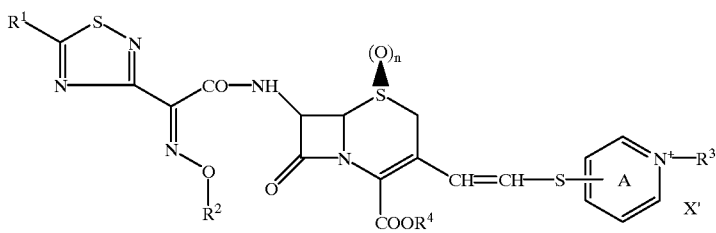

[VI]

wherein symbols are of the same meaning as defined above, followed by removing the protective group.

The nucleophilic substitution between the compound [III] and the compound [IV] can be conducted under substantially the same conditions as those for the reaction between the compound [IX] and the compound [IV] in Method (1).

To produce quaternary ammonium salt of the compound [V] by the reaction with $R^3X$ can be conducted under substantially the same conditions as those for the reaction between the compound [XI] and $R^3X$ in Method (1). The protective group on the compound [VI] thus obtained can be removed by the method described in Method (1) to lead to the compound [I] of this invention.

Method (3): A method of producing the compound described in (1) above, which is characterized by allowing, for example, a compound of the formula:

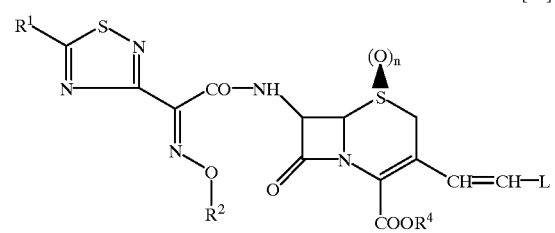

[III]

wherein symbols are of the same meaning as defined above, to react with a pyridinium compound of the formula:

[XIV]

wherein symbols are of the same meaning as defined above to give a compound of the formula [VI], followed by removing the protective group.

The reaction between the compound [III] and the compound [XIV] can be conducted under substantially the same conditions as those between the compound [IX] and the compound [IV] in Method (1) described above. The protective group on the compound [VI] thus obtained can be removed by the method described in Method (1) to obtain the compound of the formula [I] of this invention.

The compound [III] can be produced by allowing a compound of the formula:

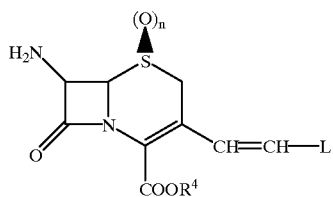

[XIII]

wherein symbols are of the same meaning as defined above, to react with carboxylic acid of the formula:

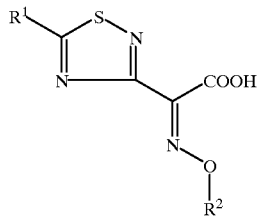

wherein symbols are of the same meaning as defined above, or a salt or reactive derivative thereof in substantially the same manner as in Method (1).

Further, the compound [XIV] in this production method can be produced by allowing the compound [IV] to react with a halogen compound represented by $R^3X$ under substantially the same conditions as those for leading the compound [XI] to the corresponding quaternary ammonium salt in Method (1).

In the above-described Methods (1) to (3), when necessary, by conducting removal of the protective group and purification, the object compound [I] of this invention can be obtained. On the method of removing the protective group and the purification method, explanation is given hereinafter.

Method of removing the protective group: As described in the foregoing, amino-protective groups have been sufficiently studied in the fields of β-lactam and peptide synthesis, and the protection method and the deprotection method have already been established. In the present invention also, for removing the protective group, conventional technique can be utilized as it is. For example, a monohalogenoacetyl group (e.g. chloroacetyl and bromoacetyl) can be removed by using thiourea; an alkoxycarbonyl group (e.g. methoxycarbonyl, ethoxycarbonyl and tert-butoxycarbonyl) can be removed by using an acid (e.g. hydrochloric acid); an aralkyloxycarbonyl group (e.g. benzyloxycarbonyl, p-methylbenzyloxycarbonyl and p-nitrobenzyloxycarbonyl) can be removed by means of catalytic reduction; and 2,2,2-trichloroethoxycarbonyl can be removed by using zinc and an acid (e.g. acetic acid). On the other hand, even in the case where the compound [I] is esterified as an intermediate for the synthesis, the ester residual group can be removed by a per se known method or an analogous method thereto. For example, 2-methylsulfonylethyl ester can be removed by using alkali; aralkyl ester (e.g. benzyl ester, benzhydryl ester, p-methoxybenzyl ester and p-nitrobenzyl ester) can be removed by using an acid (e.g. trifluoroacetic acid) or by means of catalytic reduction; 2,2,2-trichloroethyl ester can be removed by using zinc and an acid (e.g. acetic acid); and silyl ester (e.g. trimethylsilyl ester and tert-butyldimethylsilyl ester) can be removed by using only water.

For the reduction of S-oxide, a method established in the field of β-lactam can be employed, and, in the present invention also, a conventional technique can be utilized as it is. For example, phosphorus trichloride and phosphorus tribromide can be employed.

Purification of the compound [I]: The compound [I] produced in the reaction mixture by any method described in detail in Methods (1) to (3) or, depending on necessity, followed by conducting the above-mentioned removal of the protective group, can be isolated and purified by means of a conventional process such as extraction, column chromatography, precipitation and recrystallization. On the other hand, it is also possible that the compound [I] thus isolated can be converted to a desired physiologically acceptable salt by a conventional method.

The compound (I) of this invention has antibacterial activities of a broad spectrum and can be used safely for prophylaxis and therapy of various diseases, in man and mammals (e.g. mouse, rat, rabbit, dog, cat, cow and pig), caused by pathogenic bacteria, for example, respiratory infection and urinary tract infection. Characteristic features of the antibacterial spectrum of the antibacterial compound [I] are as follows, among others: (1) showing a remarkably high activity against a variety of Gram-negative bacteria, (2) having high activities against Gram-positive bacteria (e.g. *Staphylococcus aureus* and *Corynebacterium diphtheriae*), (3) having high activities against methicillin-resistant *Staphylococcus aureus* (MRSA), and (4) having high activities also against a number of β-lactamase-producing Gram-negative bacteria (e.g. genera Escherichia, Enterobacter and Proteus).

Besides, the antibacterial compound [I] of this invention has such characteristic features as (1) having excellent stability, (2) showing high concentration in blood, (3) performing long duration of effects and (4) being remarkable in tissue-transition.

The compound [I] of this invention can be administered, like known penicillin preparations or cephalosporin preparations, non-orally or orally as injectable preparations, capsules, tablets or granular preparations (injectable preparations are especially preferable). The daily dose ranges from 0.5 to 80 mg, preferably from 2 to 40 mg relative to 1 kg of the body weight of a man or an animal infected with pathogenic bacteria as described above, which may be administered in two to three divided doses. As carriers for injectable preparations, use is made of, for example, distilled water or a physiological saline solution, and, carriers for capsules, powdery preparations, granular preparations or tablets are used as a mixture with known pharmaceutically acceptable excipients (e.g. starch, maltose, sucrose, calcium carbonate or calcium phosphate), binders (e.g. starch, gum arabic, carboxymethyl cellulose, hydroxypropyl cellulose or crystalline cellulose), lubricants (e.g. magnesium stearate or talc) and disintegrants (e.g. carboxymethyl calcium and talc). Incidentally, the medicinal composition and antibacterial composition employed in the present specification may contain the compound [I] alone, or contain, among others, such carriers as set forth above, or contain a proper amount of any other adequate antibacterial compound.

EXAMPLES

The present invention will be illustrated in further detail in the following Working Examples, which are mere examples and do not limit this invention, and may be modified within the range not deviating from the scope of this invention.

Elution in the column chromatography conducted in Working Examples was carried out while monitoring with TLC (Thin Layer Chromatography). In the TLC monitoring, as the TLC plate, use was made of 60F254 manufactured by Merck & Co., Inc., as the developing solvent, use was made of the same solvent as employed for eluting in the column chromatography, and the detection was conducted with a UV detector. The silica gel for the column was Kieselgel 60 manufactured by manufactured by Merck & Co. Inc. (70 to 230 mesh). "Sephadex" is a product of Pharmacia Fine Chemicals. XAD-2 resin is a product of Rohm & Haas Co. Diaion HP20 is a product of Mitsubishi Chemical Industries, Ltd. NMR spectra were measured using tetramethylsilane as an internal or external standard with a spectrometer Gemini 200 and all delta values were expressed in ppm. The value shown in ( ) for a mixed solvent is a mixing ratio in volume of constituent solvents. The percent (%) for a solution indicates the number of grams in 100 ml of the solution. And, the symbols in Reference Examples and Working Examples have the following meaning.

s: singlet d: doublet t: triplet q: quartet

ABq: AB type quartet dd: double doublet m : multiplet bs: broad singlet

J: coupling constant

Working Example 1

7β-[2-(5-Amino-1,2,4-thiadiazol-3-yl)-2(Z)-fluoromethoxyiminoacetamide]-3-[(E)-2-(1-carbamoylmethyl-4-pyridinio)thio]vinyl-3-cephem-4-carboxylate In 4 ml of dimethylformamide was dissolved 430 mg of 7β-t-butoxycarbonylamino-3-[(E)-2-(4-pyridyl)thio]vinyl-3-cephem-4-carboxylic acid benzhydryl ester. To the solution was added 4.0 g of iodoacetamide, and the mixture was stirred for 15 hours at room temperature (about 25° C.). To the reaction mixture was added ethyl ether. Resulting oily precipitate was taken and dissolved in a mixture of 4 ml of anisole and 5 ml of trifluoroacetic acid. The mixture was stirred for 1.5 hour at room temperature. To the reaction mixture was added 60 ml of ethyl ether. Resulting precipitate was collected by filtration, which was dried under reduced pressure to give 500 mg of 7β-amino-3-[(E)-2-(1-carbamoylmethyl-4-pyridinio)thio]vinyl-3-cephem-4-carboxylate ditrifluoroacetate. In 20 ml of a mixture of tetrahydrofuran:water (1:1) was dissolved 140 mg of this compound, whose pH was adjusted to 7.5 with an aqueous solution of sodium hydrogencarbonate. To this solution was added 80 mg of 2-(5-amino-1,2,4-thiadiazol-3-yl)-2(Z)-fluoromethoxyiminoacetyl chloride hydrochloride, which was stirred for 15 minutes at 0° C. while adjusting the pH at 8 with an aqueous solution of sodium hydrogencarbonate. The reaction mixture was concentrated, which was subjected to an MCI gel CHP-20P columm chromatography. Fractions eluted with 10% aqueous solution of ethanol were collected and concentrated. The concentrate was lyophilized to give 41 mg of the titled compound.

Elemental Analysis for $C_{21}H_{19}N_8O_6S_3F \cdot 4H_2O$:

Calcd.: C, 37.83; H, 4.08; N, 16.81

Found : C, 37.90; H, 4.06; N, 16.71

NMR(DMSO-$d_6$, δ): 3.68(2H,m), 5.11(1H,d,J=4.4 Hz), 5.25(2H,bs), 5.66(1H,m), 5.80(2H,d,J=56 Hz), 6.55&7.55(each 1H,d,J=16 Hz), 8.01&8.63(each 2H,d,J=6.6 Hz), 8.25(2H,bs), 9.79(1H,d,J=8.0 Hz)

Working Example 2

7β-[2-(5-Amino-1,2,4-thiadiazol-3-yl)-2(Z)-fluoromethoxyiminoacetamido)-3-[(E)-2-(1-methyl-4-pyridinio)thio]vinyl-3-cephem-4-carboxylate In 30 ml of a mixture of tetrahydrofuran:water (1:1) was dissolved 199 mg of 7β-amino-3-[(E)-2-(1-methyl-4-pyridinio)thio]vinyl-3-cephem-4-carboxylate ditrifluoroacetate. The solution was adjusted to pH 7.5 with an aqueous solution of sodium hydrogencarbonate. To this solution was added 120 mg of 2-(5-amino-1,2,4-thiadiazol-3-yl)-2(Z)-fluoromethoxyiminoacetyl chloride hydrochloride, while adjusting the pH at 8 under ice-cooling with an aqueous solution of sodium hydrogencarbonate. The mixture was stirred for 20 minutes at 0° C. The reaction mixture was concentrated, which was subjected to an MCI gel CHP-20P column chromatography. Fractions eluted with a 20% aqueous solution of ethanol were collected and concentrated under reduced pressure, which was lyophilized to give 111 mg of the titled compound.

Elemental Analysis for $C_{20}H_{18}N_7O_5S_3F \cdot 4.5H_2O$:

Calcd.: C, 37.97; H, 4.30; N, 15.50

Found : C, 37.93; H, 4.19; N, 15.39

NMR(DMSO-$d_6$, δ): 3.56&3.79(each 1H,d,J=17.0 Hz), 4.19(3H,s), 5.10(1H,d,J=5.2 Hz), 5.67(1H,dd,J=8.4&5.2 Hz), 5.80(2H,d,J=54 Hz), 6.50&7.52(each 1H,d,J=15.4 Hz), 7.97&8.66(each 2H,d,J= 6.6 Hz), 8.25(2H,bs), 9.78(1H,d,J=8.4 Hz)

Working Example 3

7β-[2-(5-Amino-1,2,4-thiadiazol-3-yl)-2(Z)-(2-fluoroethoxyimino)acetamido]-3-[(E)-2-(1-methyl-4-pyridinio)thio]vinyl -3-cephem-4-carboxylate In 30 ml of a mixture of tetrahydrofuran:water (1:1) was dissolved 204 mg of 7β-amino-3-[(E)-2-(1-methyl-4-pyridino)thio]vinyl-3-cephem-4-carboxylate ditrifluoroacetate, whose pH was adjusted to 7.5 with an aqueous solution of sodium hydrogencarbonate. To this solution was added 151 mg of 2-(5-amino-1,2,4-thiadiazol-3-yl)-2(Z)-(2-fluoroethoxyimino)acetyl chloride hydrochloride, while adjusting the pH to 8, under ice-cooling, with an aqueous solution of sodium hydrogencarbonate. The mixture was stirred for 20 minutes at 0° C. and the reaction mixture was concentrated, which was subjected to an MCI gel CHP-20P column chromatography. Fractions eluted with a 20% aqueous solution of ethanol were collected and concentrated. The concentrate was lyophilized to give 111 mg of the titled compound.

Elemental Analysis for $C_{21}H_{20}N_7O_5S_3F \cdot 4H_2O$:
  Calcd.: C, 39.55; H, 4.43; N, 15.38
  Found : C, 39.51; H, 4.44; N, 15.05
NMR(DMSO-$d_6$, δ) : 3.55&3.78(each 1H,d,J=17.0 Hz), 4.19(3H,s), 4.39(2H,dt,J=29.2&3.6 Hz),
4.69(2H,dt,J=47.6&3.6 Hz), 5.09(1H,d,J=5.2 Hz),
5.67(1H,dd,J=8.4&5.2 Hz), 6.51&7.51(each 1H,d,J=15.4 Hz),
7.97&8.66(each 2H,d,J=6.6 Hz), 8.19(2H,bs),
9.63(1H,d,J=8.4 Hz)

Working Example 4

7β-[2-(5-Amino-1,2,4-thiadiazol-3-yl)-2(Z)-fluoromethoxyiminoacetamide]-3-[(E)-2-(1-methyl-3-pyridinio)thio]vinyl-3-cephem-4-carboxylate In 3.5 ml of dimethylformamide was dissolved 450 mg of 7β-t-butoxycarbonylamino-3-[(E)-2-(3-pyridyl)thio]vinyl-3-cephem-4-carboxylic acid benzhydryl ester. To the solution was added 1.5 ml of iodomethane, and the mixture was stirred for 13 hours at room temperature. To the reaction mixture was added 50 ml of ethyl ether. After stirring the mixture for 30 minutes, ethyl ether was removed by decantation. Resulting precipitate was dissolved in 4 ml of anisole, and 4.88 ml of trifluoroacetic acid was added. The mixture was stirred for 1 hour at room temperature. To the reaction mixture was added 60 ml of ethyl ether. Resulting precipitate was collected by filtration.

The precipitate was dissolved in a mixture (60 ml) of tetrahydrofuran-water (1:1). To this solution were added 256 mg of sodium hydrogencarbonate and 233 mg of 2-(5-amino-1,2,4-thiadiazol-3-yl)-2(Z)-fluoromethoxyiminoacetyl chloride hydrochloride under ice cooling. The mixture was stirred for 30 minutes at 0° C. After adding 100 ml of water, the reaction mixture was concentrated, which was subjected to an MCI gel CHP-20P columm chromatography. Fractions eluted with 15% aqueous solution of ethanol were collected and concentrated. The concentrate was lyophilized to give 168 mg of the titled compound.

Elemental Analysis for $C_{20}H18N_7O_5S_3F \cdot 3.5H_2O$:
  Calcd.: C, 39.08; H, 4.10; N, 15.95
  Found : C, 38.85; H, 4.16; N, 15.65
NMR(DMSO-$d_6$, δ): 3.54(1H,d,J=16.6 Hz),
3.74(1H,d,J=16.6 Hz), 4.34(3H,s), 5.09(1H,d,J=5.0 Hz),
5.66(1H,dd,J=8.0&5.0 Hz), 5.79(2H,d,J=56.0 Hz),
6.46&7.50(each 1H,d,J=15.0 Hz), 8.00(1H,dd,J=8.0&5.8 Hz),
8.23(2H,bs), 8.47(1H,d,J=8.0 Hz), 8.78(1H,d,J=5.8 Hz),
8.98(1H,s), 9.76(1H,d,J=8.0 Hz).

Working Example 5

7β-[2-(5-Amino-1,2,4-thiadiazol-3-yl)-2(Z)-fluoromethoxyiminoacetamide]-3-[(E)-2-(1-methyl-2-pyridinio)thio]vinyl-3-cephem-4-carboxylate In 4.2 ml of dimethylformamide was dissolved 545 mg of 7β-t-butoxycarbonylamino-3-[(E)-2-(2 -pyridyl)thio]vinyl-3-cephem-4-carboxylic acid benzhydryl ester. To the solution was added 1.86 ml of iodomethane, and the mixture was stirred for 20 hours at room temperature. To the reaction mixture was added 50 ml of ethyl ether. After stirring the mixture for 30 minutes, ethyl ether was removed by the decantation. Resulting precipitate was dissolved in 4 ml of anisole, and 4.88 ml of trifluoroacetic acid was added. The mixture was stirred for 1.5 hour at room temperature. To the reaction mixture was added 60 ml of ethyl ether. Resulting precipitate was collected by filtration, which was dried under reduced pressure to give 255 mg of 7β-amino-3-[(E)-2-(1-methyl-2-pyridinio)thio]vinyl-3-cephem-4-carboxylate.

The compound was dissolved in a mixture (40 ml) of tetrahydrofuran-water (1:1). To this solution were added 167 mg of sodium hydrogencarbonate and 152 mg of 2-(5-amino-1,2,4-thiadiazol-3-yl)-2(Z)-fluoromethoxyiminoacetyl chloride hydrochloride under ice cooling. The mixture was stirred for 30 minutes at 0° C. After adding 100 ml of water, the reaction mixture was concentrated, which was subjected to an MCI gel CHP-20P columm chromatography. Fractions eluted with 15% aqueous solution of ethanol were collected and concentrated. The concentrate was lyophilized to give 100 mg of the titled compound.

Elemental Analysis for $C_{20}H_{18}N_7O_5S_3F \cdot 4.0H_2O$:
  Calcd.: C, 38.52; H, 4.20; N, 15.72
  Found : C, 38.44; H, 4.12; N, 15.51
NMR(DMSO-$d_6$, δ): 3.58(1H,d,J=16.6 Hz),
3.79(1H,d,J=16.6 Hz), 4.18(3H,s), 5.12(1H,d,J=5.0 Hz),
5.70(1H,dd,J=8.4&5.0 Hz), 5.80(2H,d,J=56.0 Hz),
6.42&7.67(each 1H,d,J=15.0Hz), 7.77(1H,dd,J=7.0&5.8 Hz),
8.04(1H,d,J=8.0Hz), 8.24(2H,bs),
8.35(1H,dd,J=8.0&7.0 Hz), 8.94(1H,d,J=5.8 Hz),
9.78(1H,d,J=8.4 Hz).

Working Example 6

7β-[2-(5-Amino-1,2,4-thiadiazol-3-yl)-2(Z)-fluoromethoxyiminoacetamide]-3-((E)-2-(1-carbamoylmethyl-2-pyridinio)thio]vinyl-3-cephem-4-carboxylate In 1.3 ml of dimethylformamide was dissolved 183 mg of 7β-t-butoxycarbonylamino-3-[(E)-2-(2-pyridyl)thio]vinyl-3-cephem-4-carboxylic acid benzhydryl ester. To the solution was added 1.69 g of iodoacetamide, and the mixture was stirred in an oil bath for 90 hours at 40° C. To the reaction mixture was added 26 ml of ethyl ether. After stirring the mixture for 30 minutes, ethyl ether was removed by the decantation. Resulting precipitate was dissolved in 1.7 ml of anisole, and 2.1 mol of trifluoroacetic acid was added. The mixture was stirred for 1.5 hour at room temperature. To the reaction mixture was added 25 ml of ethyl ether. The ethyl ether was removed by decantation.

The compound was dissolved in a mixture (30 ml) of tetrahydrofuran-water (1:1). To this solution were added 87 mg of sodium hydrogencarbonate and 80.8 mg of 2-(5-amino-1,2,4-thiadiazol-3-yl)-2(Z)-fluoromethoxyiminoacetyl chloride hydrochloride under ice cooling. The mixture was stirred for 30 minutes at 0° C. After adding 100 ml of water, the reaction mixture was concentrated, which was subjected to an MCI gel CHP-20P columm chromatography. Fractions eluted with 15% aqueous solution of ethanol were collected and concentrated. The concentrate was lyophilized to give 47.8 mg of the titled compound.

Elemental Analysis for $C_{21}H_{19}N_8O_6S_3F\cdot 4.5H_2O$:
  Calcd.: C, 37.33; H, 4.18; N, 16.58
  Found : C, 37.35; H, 3.89; N, 16.63
NMR(DMSO-$d_6$, δ): 3.71(2H,m), 5.14(1H,d,J=5.0 Hz), 5.37(2H,bs), 5.74(1H,dd,J=8.0&5.0 Hz), 5.80(2H,d,J=56.0 Hz), 6.51&7.59(each 1H,d,J=15.0 Hz), 7.82&8.24(each 1H,bs), 7.86(1H,dd,J=7.0&5.8 Hz), 8.10(1H,d,J=8.6 Hz), 8.23(2H,bs), 8.43(1H,dd,J=8.6&7.0 Hz), 8.88(1H,d,J=5.8 Hz), 9.82(1H,d,J=8.0Hz).

Working Example 7

7β-[2-(5-Amino-1,2,4-thiadiazol-3-yl)-2(Z)-(2-fluoroethoxy)iminoacetamide]-3-[(E)-2-(1-methyl-2-pyridinio)thio]vinyl-3-cephem-4-carboxylate In 40 ml of a mixture of tetrahydrofuran-water (1:1) was dissolved 250 mg of 7β-amino-3-[(E)-2-(1-methyl-2-pyridinio)thio]vinyl-3-cephem-4-carboxylate·hydriodic acid·trifluoroacetate. To this solution were added 167 mg of sodium hydrogenecarbonate and 162 mg of 2-(5-amino-1,2,4-thiadiazol-3-yl)-2(Z)-(2-fluoroethoxy)iminoacetyl chloride hydrochloride under ice cooling. The mixture was stirred for 30 minutes at 0° C. After adding 100 ml of water, the reaction mixture was concentrated, which was subjected to an MIC gel CHP-20P column chromatography. Fractions eluted with 15% aqueous solution of ethanol were collected and concentrated. The concentrate was lyophilized to give 119 mg of the titled compound. Elemental Analysis for $C_{21}H_{20}N_7O_5S_3F\cdot 3.5H_2O$:
  Calcd.: C, 40.12; H, 4.33; N, 15.60
  Found : C, 39.88; H, 4.03; N, 15.38
NMR(DMSO-$d_6$, δ): 3.59(1H,d,J=16.8 Hz), 3.83(1H,d,J=16.8 Hz), 4.18(3H,s), 4.39(2H,dt,J=29.2&3.6 Hz), 4.69(2H,dt,J=47.6&3.6 Hz), 5.13(1H,d,J=5.0 Hz), 5.72(1H,dd,J=8.4&5.0 Hz), 6.50&7.63(each 1H,d,J=15.0 Hz), 7.78(1H,dd,J=7.0&5.8 Hz), 8.06(1H,d,J=8.0 Hz), 8.21(2H,bs), 8.35(1H,dd,J=8.0&7.0 Hz), 8.95(1H,d,J=5.8 Hz), 9.66(1H,d,J=8.4 Hz).

Working Example 8

7β-(2-(5-Amino-1,2,4-thiadiazol-3-yl)-2(Z)-(2-fluoroethoxy)iminoacetamide]-3-[(E)-2-(1-carbamoylmethyl-2-pyridinio)thiolvinyl-3-cephem-4-carboxylate In 1.3 ml of dimethylformamide was dissolved 183 mg of 7β-t-butoxycarbonylamino-3-[(E)-2-(2-pyridyl)thio]vinyl-3-cephem-4-carboxylic acid benzhydryl ester. To the solution was added 1.69 g of iodoacetamide, and the mixture was stirred in an oil bath for 90 hours at 40° C. To the reaction mixture was added 26 ml of ethyl ether. After stirring the mixture for 30 minutes, ethyl ether was removed by decantation.

The compound was dissolved in a mixture (30 ml) of tetrahydrofuran-water (1:1). To this solution were added 87 mg of sodium hydrogencarbonate and 84.6 mg of 2-(5-amino-1,2,4-thiadiazol-3-yl)-2(Z)-(1-fluoroethoxy)iminoacetyl chloride hydrochloride under ice cooling. The mixture was stirred for 30 minutes at 0° C. After adding 100 ml of water, the reaction mixture was concentrated, which was subjected to an MCI gel CHP-20P columm chromatography. Fractions eluted with 15% aqueous solution of ethanol were collected and concentrated. The concentrate was lyophilized to give 48.3 mg of the titled compound.
Elemental Analysis for $C_{22}H_{21}N_8O_6S_3F\cdot 4.0H_2O$:
  Calcd.: C, 38.82; H, 4.29; N, 16.46
  Found : C, 38.59; H, 3.99; N, 16.68
NMR(DMSO-$d_6$, δ): 3.59(1H,d,J=16.6 Hz), 3.80(1H,d,J=16.6 Hz), 4.39(2H,dt,J=29.8&3.6 Hz), 4.69(2H,dt,J=48.2&3.6 Hz), 5.12(1H,d,J=5.0Hz), 5.37(2H,bs), 5.72(1H,dd,J=8.0&5.0Hz), 6.49&7.59(each 1H,d,J=15.0 Hz), 7.82&8.24(each 1H,bs), 7.86(1H,dd,J=7.0&5.8 Hz), 8.10(1H,d,J=8.4 Hz), 8.18(2H,bs), 8.42(1H,dd,J=8.4&7.0 Hz), 8.88(1H,d,J=5.8 Hz), 9.66(1H,d,J=8.0 Hz).

Chemical Structural formulae of the compounds in the Working Examples are as follows:

Compound of Working Example 1

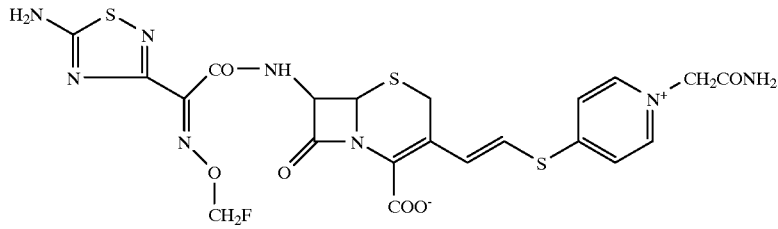

Compound of Working Example 2

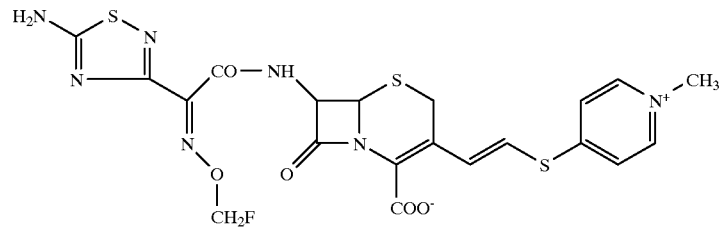

-continued
Compound of Working Example 3
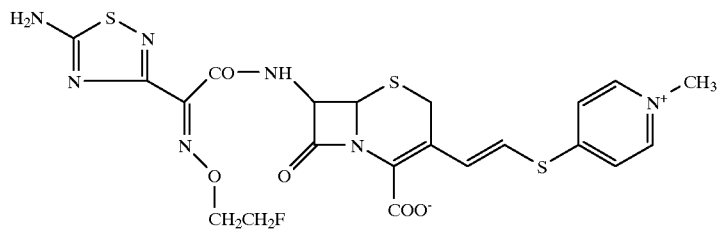
Compound of Working Example 4
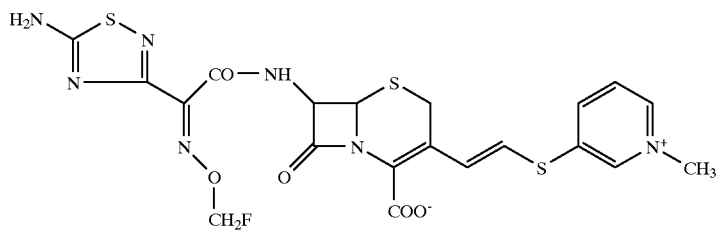
Compound of Working Example 5
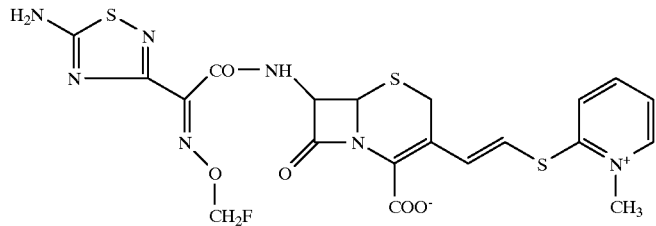
Compound of Working Example 6
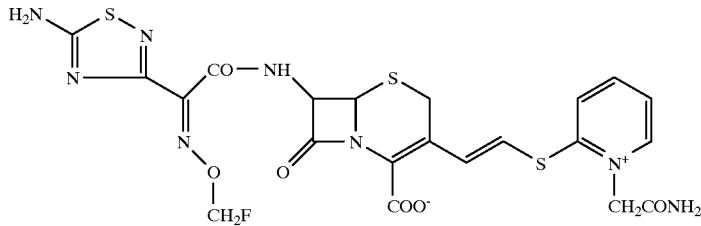
Compound of Working Example 7
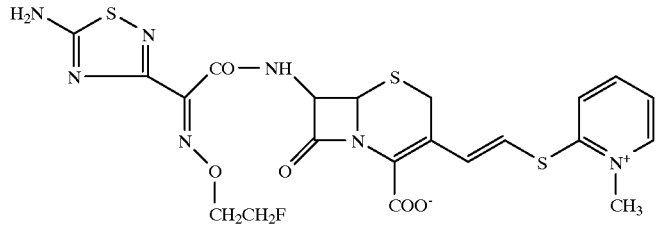

-continued

Compound of Working Example 8

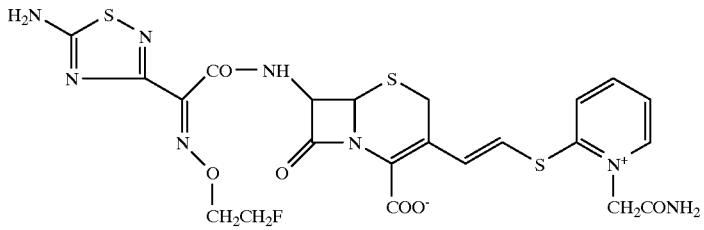

The cephem compounds [I] or their esters or salts have a broad antibacterial spectrum and an excellent antibacterial activity against Gram-negative bacterial including those belonging to the genus Pseudomonas and Gram-positive bacteria including *Staphylococcus aureus* and MRSA. Thus, antibacterial agents effective against infectious diseases caused by these bacteria are provided.

We claim:
1. A compound of the formula:

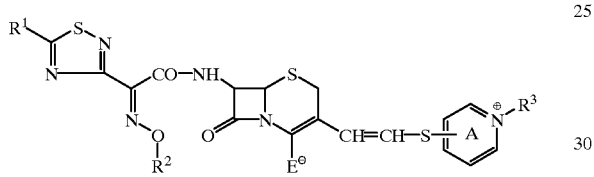

wherein
$R^1$ is an optionally protected amino group;
$R^2$ is a fluoro-lower alkyl group;
$R^3$ is a
   (a) a $C_{1-6}$alkyl group,
   (b) a $C_{2-6}$alkenyl group,
   (c) a $C_{2-6}$alkynyl group,
   (d) a $C_{7-19}$aralkyl group,
   (e) a 3- to 7-membered non-aromatic cyclic hydrocarbon group or
   (f) a $C_{6-10}$aryl group,
   wherein each of the above groups (a) to (f) may be substituted with one to four substituents selected from the group consisting of
   1) a heterocyclic group which is a 5- to 8-membered ring containing 1 to 4 hetero-atoms selected from nitrogen which may be oxidized, oxygen or sulfur, or condensed ring selected from the group consisting of 3H-indol-2-yl, 3H-indol-3-yl, benzopyranyl, quinolyl, pyrido[2,3-d]pyrimizyl, 1,5-naphthyridyl, 1,6-naphthyridyl, 1,7-naphthyridyl, 1,8-naphthyridyl, 2,6-naphthyridyl, 2,7-naphthyridyl, thieno[2,3-d]pyridyl, pyrimidopyridyl, pyrazinoquinolyl and benzopryanyl,
   2) a hydroxyl group,
   3) a $C_{3-10}$cycloalkyl group,
   4) a $C_{1-6}$alkoxy group,
   5) a $C_{3-7}$cycloalkyloxy group,
   6) a $C_{6-10}$aryloxy group,
   7) a $C_{7-19}$aralkyloxy group,
   8) a heterocyclic-oxy group whose heterocyclic moiety is a 5- to 8-membered ring containing 1 to 4 hetero-atoms selected from nitrogen which may be oxidized, oxygen or sulfur, or condensed ring selected from the group consisting of 3H-indol-2-yl, 3H-indol-3-yl, benzopyranyl, quinolyl, prido[2,3-d]pyrimidyl, 1,5-naphthridyl, 1,6-naphthyridyl, 1,7-naphthyridyl, 1,8-naphthyridyl, 2,6-naphthyridyl, 2,7-naphthyridyl, thieno[2,3-d]pyridyl, pyrimidopyridyl, pyrazinoquinolyl and benzopyranyl,
   9) a mercapto group,
   10) a $C_{1-6}$alkylthio group,
   11) a $C_{3-10}$cycloalkylthio group,
   12) a $C_{6-10}$-arylthio group,
   13) a $C_{7-19}$-aralkylthio group,
   14) a heterocyclic thio group whose heterocyclic moiety is a 5- to 8-membered ring containing 1 to 4 hetero-atoms selected from nitrogen which may be oxidized, oxygen or sulfur, or condensed ring selected from the group consisting of 3H-indol-2-yl, 3H-indol-3-yl, benzopyranyl, quinolyl, pyrido[2,3-d]pyrimidyl, 1,5-naphthyridyl, 1,6-naphthyridyl, 1,7-naphthyridyl, 1,8-naphthyridyl, 2,6-naphthridyl, 2,7-naphthyridyl, thieno[2,3-d]pyridyl, pyrimidopyridyl, pyrazinoquinolyl and benzopyranyl,
   15) an amino group,
   16) a mono-$C_{1-6}$alkylamino group,
   17) a di-$C_{1-6}$alkylamino group,
   18) a $C_{7-19}$aralkyloxy-carboxamido group,
   19) a $C_{3-10}$cycloalklamino group,
   20) a $C_{6-10}$arylamino group,
   21) a $C_{7-19}$aralkylamino group,
   22) a heterocyclic amino group whose heterocyclic moiety is a 5- to 8-membered ring containing 1 to 4 hetero-atoms selected from nitrogen which may be oxidized, oxygen or sulfur, or condensed ring selected from the group consisting of 3H-indol-2-yl, 3H-indol-3-yl, benzopyranyl, quinolyl, pyrido[2,3-d]pyrimidyl, 1,5-naphthyridyl, 1,6-naphthyridyl, 1,7-naphthyridyl, 1,8naphthyridyl, 2,6-naphthyridyl, 2,7naphthyridyl, thieno[2,3-d]pyridyl, pyrimidopyridyl, pyrazinoquinolyl and benzopyranyl,
   23) a cyclic amino group selected from the group consisting of pyrrolidino, piperidino, piperazino, morpholino and 1-pyrrolyl,
   24) an azido group,
   25) a nitro group,
   26) a halogen atom,
   27) a cyano group,
   28) a carboxyl group,
   29) a $C_{1-10}$alkoxy-carbonyl group,
   30) a $C_{1-10}$aryloxy-carbonyl group,
   31) a $C_{7-19}$aralkyloxy-carbonyl group,
   32) a $C_{6-10}$aryl-carbonyl group, 33) a $C_{1-6}$alkanoyl group,
34) a $C_{3-5}$alkenoyl group,
35) a $C_{6-10}$aryl-carbonyloxy group,
36) a $C_{2-6}$alkanoyloxy group,
37) a $C_{3-5}$alkenoyloxy group,
38) a carbamoyl group optionally substituted with one of two substituents selected from a group consisting of a $C_{1-6}$alkyl group, a $C_{1-6}$alkanoyl group, a $C_{6-10}$arylcarbonyl group and a $C_{1-6}$ alkoxy-phenyl group,
39) an cyclic aminocarbonyl group selected from the group consisting of a pyrrolidinocarbonyl group, a piperidinocarbonyl group, a piperazinocarbonyl group and a morpholinocarbonyl group, each of which may be substituted with one or two substituents selected from a group consisting of a $C_{1-6}$alkyl group, a $C_{1-4}$alkanoyl group, a $C_{6-10}$arylcarbonyl group and a $C_{1-6}$alkoxy-phenyl group,
40) a thiocarbamoyl group optionally substituted with one or two substituents selected from a group consisting of a $C_{1-6}$alkyl group and a $C_{6-10}$aryl group,
41) a carbamoyloxy group optionally substituted with one or two substituents selected from the group consisting of a $C_{1-6}$alkyl group and a $C_{6-10}$aryl group,
42) a phthalimido group,
43) a $C_{1-6}$alkanoylamino group,
44) a $C_{6-10}$aryl-carbonylamino group,
45) a $C_{1-10}$alkoxy-carboxamido group, and
46) a $C_{6-10}$aryloxy-carboxamido group, and the ring A may optionally have, at any possible position, one or two substituents selected from the group consisting of 1) a hydroxyl group,
2) a hydroxy $C_{1-6}$alkyl group,
3) a $C_{1-6}$alkyl group,
4) a $C_{2-6}$alkenyl group,
5) a $C_{2-6}$alkynyl group,
6) a $C_{3-10}$cycloalkyl group,
7) a $C_{3-6}$cycloalkenyl group,
8) a $C_{3-10}$cycloalkyl-$C_{1-6}$alkyl group,
9) a $C_{6-10}$aryl group,
10) a $C_{7-12}$aralkyl group,
11) a heterocyclic group which is a 5- to 8-membered ring containing 1 to 4 hetero-atoms selected from nitrogen which may be oxidized, oxygen or sulfur, or condensed ring selected from the group consisting of 3H-indol-2-yl, 3H-indol-3-yl, benzopyranyl, quinolyl, pyrido[2,3-d]pyrimidyl, 1,5-naphthyridyl, 1,6-naphthyridyl, 1.7-naphthyridyl, 1.0-naphthyridyl, 2,6-naphthyridyl, 2,7-naphthyridyl, thieno[2,3-d]pyridyl, pyrimidopyridyl, pyrazinoquinolyl and benzopyranyl,
12) a $C_{1-6}$alkoxy group,
13) a $C_{1-6}$alkoxy-$C_{1-6}$alkyl group,
14) an amino-$C_{1-6}$alkoxy group,
15) a $C_{3-10}$cycloalkyloxy group,
16) a $C_{6-10}$aryloxy group,
17) a $C_{7-19}$aralkyloxy group,
18) a mercapto group,
19) a mercapto-$C_{1-6}$alkyl group,
20) a sulfo group,
21) a sulfo-$C_{1-6}$alkyl group,
22) a $C_{1-6}$alkylthio group,
23) a $C_{1-6}$alkylthio $C_{2-6}$alkyl group,
24) a $C_{3-10}$cycloalkylthio group,
25) a $C_{6-10}$arylthio group,
26) a $C_{7-19}$aralkylthio group,
27) an amino-$C_{1-6}$alkyl group,
28) an amino group,
29) an amino-$C_{1-6}$alkyl group,
30) a mono-$C_{1-6}$alkylamino group,
31) a di-$C_{1-6}$alkylamino group,
32) a mono-$C_{1-6}$alkylamino-$C_{1-6}$alkyl group,
33) a di-$C_{1-6}$alkylamino-$C_{1-6}$alkyl group,
34) a $C_{3-10}$cycloalkylamino group,
35) a $C_{6-10}$arylamino group,
36) a $C_{7-19}$aralkylamino group,
37) a cyclic amino group selected from the group consisting of pyrrolidino, piperidino, piperazino, morpholino and 1-pyrrolyl,
38) a cyclic amino-$C_{1-6}$alkyl group selected from the group consisting of pyrrolidinomethyl, piperidinomethyl, piperazinomethyl, morpholinomethyl and 2-(morpholino)ethyl
39) a cyclic amino-$C_{1-6}$alkylamino group, pyrrolidinoethylamino, piperidinoethylamino, piperazinoethylamino and morpholinoethylamino,
40) an acylamino group whose acyl moiety is selected from the group consisting of $C_{1-6}$alkanoyl group $C_{3-10}$alkenoyl group, $C_{3-10}$cycloalkyl-carbonyl group, $C_{5-6}$cycloalkenyl-carbonyl group, $C_{6-10}$aryl-carbonyl group, $C_{7-19}$ aralkyl-carbonyl group, amino $C_{1-6}$ alkyl-carbonyl group, di-$C_{1-6}$alkylamino-$C_{1-6}$alkyl-carbyonyl group, cyclic aminoalkylcarbonyl group selected from the group consisting of imidazolinomethylcarbonyl and pyrazolinoethylcarbonyl, and an amine acid residue formed by removing hydroxyl group of carboxyl group of amine acid,
41) an ureido group,
42) a $C_{1-6}$alkylureido group,
43) an azido group,
44) nitro group,
45) a halogen atom,
46) a halogen-$C_{1-6}$alkyl group,
47) a cyano-group,
48) a cyano-$C_{1-6}$alkyl group,
49) a carboxyl group,
50) a carboxy-$C_{1-6}$alkyl group,
51) a $C_{1-10}$alkoxy-carbonyl-group,
52) a $C_{1-10}$alkoxy-carbonyl-$C_{1-6}$alkyl group,
53) a $C_{6-10}$aryloxyl-carbonyl group,
54) a $C_{7-19}$aralkyloxy-carbonyl group,
55) a $C_{6-10}$aryl-$C_{1-6}$alkanoyl group,
56) a $C_{1-6}$alkanoyl group,
57) a $C_{2-6}$alkanoyl-$C_{1-6}$alkyl group,
58) a $C_{3-5}$alkenoyl group,
59) a $C_{6-10}$aryl-$C_{1-6}$alkanoyloxy group,
60) a $C_{2-6}$alkanoyloxy group,
61) a $C_{2-6}$alkanoyloxy-$C_{1-6}$alkyl group,
62) a $C_{3-5}$alkenoyloxy group,
63) a carbamoyl-$C_{1-6}$alkyl group,
64) a carbamoyl group, 65) a thiocarbamoyl group,
66) a carbamoyloxy group,
67) a carbamoyloxy-$C_{1-6}$alkyl group,
68) a $C_{1-6}$alkanoylamino group,
69) a $C_{6-10}$aryl-$C_{1-6}$alkanoylamino group,
70) a sulfonamido group,
71) a carboxamido group,
72) a $C_{1-10}$alkoxy-carboxamido group,
73) a $C_{6-10}$aryloxy-carboxamido group, and
74) a $C_{7-19}$aralkyloxy-carboxamido group, and
$E^{63}$ is $COO^{\ominus}$.

2. A compound as claimed in claim 1, which is a compound of the formula:

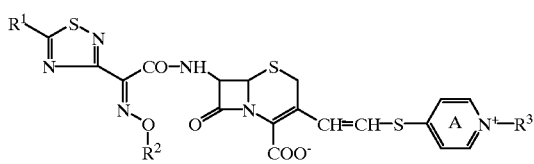

wherein each symbol has the same meaning as defined in claim 1, or an ester or salt thereof.

3. A compound as claimed in claim 1, wherein $R^1$ is amino.

4. A compound as claimed in claim 1, wherein $R^2$ is fluoromethyl.

5. A compound as claimed in claim 1, wherein $R^2$ is 2-fluoroethyl.

6. A compound as claimed in claim 1, wherein $R^3$ is an optionally substituted $C_{16}$ alkyl group.

7. A compound as claimed in claim 1, wherein the heterocyclic group or the heterocyclic moiety is a 5- to 8-membered ring selected from the group consisting 2- or 3-pyrrolyl; 3-, 4- or 5-pyrazolyl; 2-, 4- or 5-imidazolyl; 1,2,3- or 1,2,4-triazolyl; 1H- or 2H-tetrazolyl; 2- or 3-furyl; 2- or 3-thienyl; 2-, 4- or 5-oxazolyl; 3,4- or 5-isoxazolyl; 1,2,3-oxadiazol-4-yl or 1,2,3-oxadiazol-5-yl; 1,2,4-oxadiazol-3-yl or 1,2,4-oxadiazol-5-yl; 1,2,5- or 1,3,4-oxadiazolyl; 2-, 4- or 5-thiazolyl; 3-, 4- or 5-isothiazolyl; 1,2,3-thiadiazol-4-yl or 1,2,3-thiadiazol-5-yl; 1,2,4-thiadiazol-3-yl or 1,2,4-thiadiazol-5-yl; 1,2,5- or 1,3,4-thiadiazolyl; 2- or 3-pyrrolidinyl; 2-, 3- or 4-pyridyl; 2-, 3- or 4-pyridyl-N-oxido; 3- or 4-pyridazinyl; 3- or 4-pyridazinyl-N-oxido; 2-, 4- or 5-pyrimidinyl; 2-, 4- or 5-pyrimidinyl-N-oxido; pyrazinyl; 2-, 3- or 4-piperidinyl; piperazinyl; 3H-indol-2-yl or 3H-indol-3-yl; 2-, 3- or 4-pyranyl; 2-, 3- or 4-thiopyranyl; benzopyranyl; quinolyl; pyrido[2,3-d]pyrimidyl; 1,5-, 1,6-, 1,7-, 1,8-, 2,6- or 2,7-naphthyridyl; thieno[2,3-d]pyridyl; pyrimidopyridyl; pyrazinoquinolyl; and benzopyranyl.

8. A compound as claimed in claim 6, wherein the substituent of the optionally substituted $C_{1-6}$alkyl group is selected from the group consisting of hydroxyl group, $C_{3-10}$cycloalkyl groups, $C_{1-6}$alkoxy group, $C_{1-6}$alkylthio group, amino group, halogen atom, carboxyl group, $C_{1-10}$alkoxycarbonyl group, a carbamoyl group optionally substituted with one or two substituents selected from the group consisting of a $C_{1-6}$alkyl group, a $C_{1-6}$alkanoyl group, a $C_{6-10}$arylcarbonyl group and a $C_{1-6}$alkoxy-phenyl group, a cyclic aminocarbonyl group selected from the group consisting of a pyrrolidinocarbonyl group, a piperidinocarbonyl group, a piperazinocarbonyl group and a morpholinocarbonyl group, each of which may be substituted with one or two substituents selected from the group consisting of a $C_{1-6}$alkyl group, a $C_{1-6}$alkanoyl group, a $C_{6-10}$arylcarbonyl group and a $C_{1-6}$alkoxy-phenyl group, cyano group, azido group and a heterocyclic group which is 5 to 8-membered ring containing 1 to 4 hetero atoms selected from nitrogen which may be oxidized, oxygen and sulfur, or a condensed ring selected from the group consisting of 3H-indol-2-yl, 3H-indol-3-yl, benzopyranyl, quinolyl, pyrido(2,3-d)pyrimidyl, 1,5-naphthyridyl, 1,6-naphthyridyl, 1,7-naphthyridyl, 1,8-naphthyridyl, 2,6-naphthyridyl, 2,7-naphthyridyl, thieno(2,3-d)pyridyl, pyrimidopyridyl, pyrazinoquinolyl and benzopyranyl.

9. A compound as claimed in claim 1, wherein $R^3$ is a $C_{1-3}$alkyl group.

10. A compound as claimed in claim 1, which is 7-β-[2-(5-amino-1,2,4-thiadiazol-3-yl)-2(Z)-fluoromethoxyiminoacetamido]-3-[(E)-2-(1-carbamoylmethyl-4-pyridinio)thio]vinyl-3-cephem-4-carboxylate.

11. A compound as claimed in claim 1, which is 7-β-[2-(5-amino-1,2,4-thiadiazol-3-yl)-2(Z)-fluoromethoxyiminoacetamido]-3-[(E)-2-(1-methyl-4-pyridinio)thio]vinyl-3-cephem-4-carboxylate.

12. A compound as claimed in claim 1, which is 7-β-(2-(5-amino-1,2,4-thiadiazol-3-yl)-2(Z)-(2-fluoroethoxyimino)acetamido]-3-[(E)-2-(1-methyl-4-pyridinio)thio]vinyl-3-cephem-4-carboxylate.

13. A method of producing a compound as claimed in claim 1, which comprises reacting a compound of the formula:

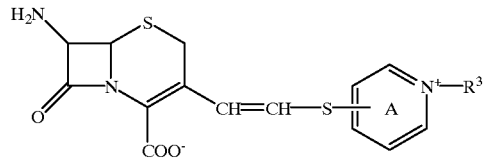

wherein the symbols have the same meanings as defined in claim 1, or an ester or salt thereof, with a carboxylic acid of the formula:

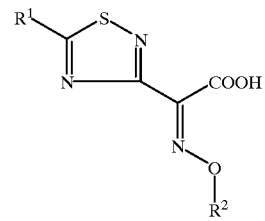

wherein the symbols have the same meanings as defined in claim 1, or a salt or reactive derivative thereof, then, if necessary, by removing the protective group.

14. A method of producing a compound as claimed in claim 1, which comprises reacting a compound of the formula:

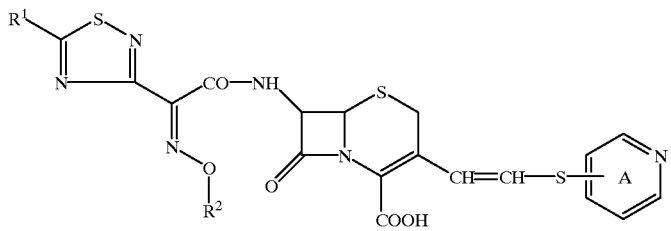

wherein the symbols have the same meanings as defined in claim 1, or an ester or salt thereof, with a compound of the formula: $R^3$—X wherein X is a leaving group and $R^3$ has the same meaning as defined in claim 1, then, if necessary, removing the protective group.

15. An antibacterial composition which comprises of a compound as claimed in claim 1 and a pharmaceutically acceptable carrier, diluent or excipient.

16. An anti-methicillin-resistant *Staphylococeus aureus* (MRSA) composition which comprises an effective amount of a compound as claimed in claim 1 and pharmaceutically acceptable carrier, diluent or excipient.

17. A method for treating or preventing bacterial infection which comprises administering an effective amount of a compound as claimed in claim 1, optionally together with a pharmaceutically acceptable carrier, diluent or excipient to a patient suffering from bacterial infection.

* * * * *